(12) United States Patent
Alisi et al.

(10) Patent No.: US 8,686,147 B2
(45) Date of Patent: Apr. 1, 2014

(54) COMPOUND WITH SEROTONINERGIC ACTIVITY, PROCESS FOR PREPARING IT AND PHARMACEUTICAL COMPOSITION COMPRISING IT

(75) Inventors: Maria Alessandra Alisi, Rome (IT); Nicola Cazzolla, Albano Laziale (IT); Roberta Costi, Rome (IT); Roberto Di Santo, Rome (IT); Guido Furlotti, Rome (IT); Angelo Guglielmotti, Rome (IT); Lorenzo Polenzani, Grottaferrata (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 340 days.

(21) Appl. No.: 13/003,809

(22) PCT Filed: Jul. 17, 2009

(86) PCT No.: PCT/EP2009/059216
§ 371 (c)(1),
(2), (4) Date: Mar. 2, 2011

(87) PCT Pub. No.: WO2010/012611
PCT Pub. Date: Feb. 4, 2010

(65) Prior Publication Data
US 2011/0160201 A1    Jun. 30, 2011

(51) Int. Cl.
*A61K 31/437* (2006.01)
*C07D 471/06* (2006.01)

(52) U.S. Cl.
USPC ............................. 546/84; 546/81; 514/292

(58) Field of Classification Search
USPC ...................... 546/81, 84; 514/292
See application file for complete search history.

(56) References Cited

U.S. PATENT DOCUMENTS

| 4,268,513 A | 5/1981 | Shapiro |
| 4,350,814 A | 9/1982 | Shapiro |
| 4,440,768 A | 4/1984 | Shapiro |
| 5,908,932 A | 6/1999 | Shaw et al. |
| 6,323,216 B1 | 11/2001 | Makovec et al. |
| 6,335,346 B1 | 1/2002 | Fourtillan et al. |
| 6,413,978 B1 | 7/2002 | Makovec et al. |

FOREIGN PATENT DOCUMENTS

| EP | 1 018 512 | 7/2000 |
| JP | 2005 306774 | 11/2005 |
| WO | 98 05660 | 2/1998 |
| WO | 99 09029 | 2/1999 |
| WO | 2004 101548 | 11/2004 |
| WO | 2005 013989 | 2/2005 |

OTHER PUBLICATIONS

Di Santo, R. et al., "A General Versatile Synthesis of 2H-Pyrrolo[3,4-c]Quinolines Via Tosylmethylisocyanide Reaction", ARKIVOC, vol. 5, pp. 181-195, XP-002511969, (2004).

Eglen, R. et al., "Central 5-$HT_4$ Receptors", Trends Pharmacol. Sci., vol. 16, No. 11, pp. 391-398, (Nov. 1995).

Hegde, S. et al., "Peripheral 5-$HT_4$ Receptors", The FASEB Journal, vol. 10, No. 12, pp. 1398-1407, (Oct. 1996).

Bockaert, J. et al., "5-$HT_4$ Receptors", Current Drug Targets-CNS & Neurological Disorders, vol. 3, No. 1, pp. 39-51, (2004).

Gershon, M., "Review Article: Serotonin Receptors and Transporters—Roles in Normal and Abnormal Gastrointestinal Motility", Aliment Pharmacol Ther, vol. 20, Suppl. 7, pp. 3-14, (2004).

Ashburn, M. et al., "Management of Chronic Pain", The Lancet, vol. 353, pp. 1865-1869, (May 29, 1999).

Woolf, C. et al., "Neuropathic Pain: Aetiology, Symptoms, Mechanisms, and Management", The Lancet, vol. 353, pp. 1959-1964, (Jun. 5 1999).

Scholz, J. et al., "Can We Conquer Pain?", Nature Neuroscience Supplement, vol. 5, pp. 1062-1076, (Nov. 2002).

Grossman, C. et al., "Development of a Radioligand Binding Assay for 5-$HT_4$ Receptors in Guinea-Pig and Rat Brain", BR. J. Pharmacol, vol. 109, pp. 618-624, (1993).

Bonhaus, D. et al., "The Pharmacology and Distribution of Human 5-Hydroxytryptamine$_{2B}$ (5-$HT_{2B}$) Receptor Gene Products: Comparison With 5-$HT_{2A}$ and 5-$HT_{2C}$ Receptors", British Journal of Pharmacology, vol. 115, No. 4, pp. 622-628, (1995).

(Continued)

*Primary Examiner* — Rita Desai
(74) *Attorney, Agent, or Firm* — Oblon, Spivak, McClelland, Maier & Neustadt, L.L.P.

(57) ABSTRACT

Compound of formula (I) in which R1, R2 and R3 are defined in the following description, and the pharmaceutically acceptable acid-addition or base-addition salts thereof. The invention also relates to a process and an intermediate for preparing it, and to a pharmaceutical composition comprising it. The invention also relates to the use of a novel 2H-pyrrolo [3,4-c]quinoline compound for preparing a pharmaceutical composition that is active in the treatment of disturbances of the serotoninergic system.

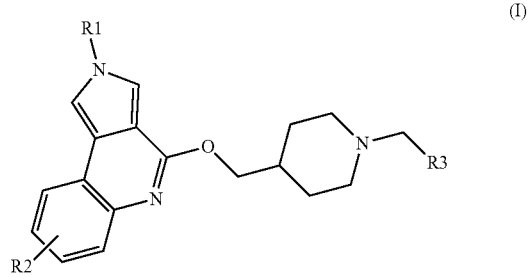

(I)

17 Claims, 1 Drawing Sheet

(56) References Cited

OTHER PUBLICATIONS

Saucier, C. et al., "Identification of an Endogenous 5-Hydroxytryptamine$_{2A}$ Receptor in NIH-3T3 Cells: Agonist-Induced Down-Regulation Involves Decreases in Receptor RNA and Number", Journal of Neurochemistry, vol. 68, No. 5, pp. 1998-2011, (1997).

Seltzer, Z. et al., "A Novel Behavioral Model of Neuropathic Pain Disorders Produced in Rats by Partial Sciatic Nerve Injury", Pain, vol. 43, pp. 205-218, (1990).

Bennett, G. et al., "A Peripheral Mononeuropathy in Rat That Produces Disorders of Pain Sensation Like Those Seen in Man", Pain, vol. 33, pp. 87-107, (1988).

International Search Report Issued Sep. 7, 2009 in PCT/EP09/059216 filed Jul. 17, 2009.

Animal Models of Pain, C. Ma, et al., Eds., vol. 49 of Neuromethods Series, Springer Protocols, Humana Press, pp. 72-75 (2010).

G. T. Whiteside, et al., "Predictive validity of animal pain models? A comparison of the pharmacokinetic-pharmacodynamic relationship of pain drugs in rats and humans," Neuropharmacology, vol. 54, pp. 767-775 (2008).

O.-G. Berge, "Predictive validity of behavioural animal models for chronic pain," British Journal of Pharmacology, vol. 164, pp. 1195-1206 (2011).

K. Taniyama, et al., "Functions of peripheral 5-hydroxytryptamine receptors, especially 5-hydroxytryptamine$_4$ receptor, in gastrointestinal motility," J. Gastroenterol., vol. 35, pp. 575-582 (2000).

J. Tack, et al., "Gastroduodenal motility," Current Opinion in Gastroenterology, vol. 26, pp. 647-655 (2010).

G. J. Sanger, et al., "SB-207266: 5-HT$_4$ receptor antagonism in human isolated gut and prevention of 5-HT-evokded sensitization of peristalsis and increased defaecation in animal models," Neurogastroenterol. Mot., vol. 10, pp. 271-279 (1998).

B. Darblade, et al., "Piboserod (SB 207266), a selective 5-HT$_4$ receptor antagonist, reduces serotonin potentiation of neurally-mediated contractile responses of detrusor muscle," World of Urol., vol. 23, pp. 147-151 (2005).

B. Brudeli, et al., "Synthesis and pharmacological properties of a new hydrophilic orally bioavailable 5-HT$_4$ antagonist," European Journal of Medicinal Chemistry, vol. 64, pp. 629-637 (2013).

J. Bockaert, et al., "5-HT$_4$ receptors, a place in the sun: act two," Current Opinion in Pharmacology, vol. 11, pp. 87-93 (2011).

A. Tamburella, et al., "Antidepressant properties of the 5-HT$_4$ receptor partial agonist, SL65.0155: Behavioral and neurochemical studies in rats," Progress in Neuro-Psychopharmacology & Biological Psychiatry, vol. 33, pp. 1205-1210 (2009).

"Neuropathic Pain," ACNR, vol. 3, pp. 8-14 (2003).

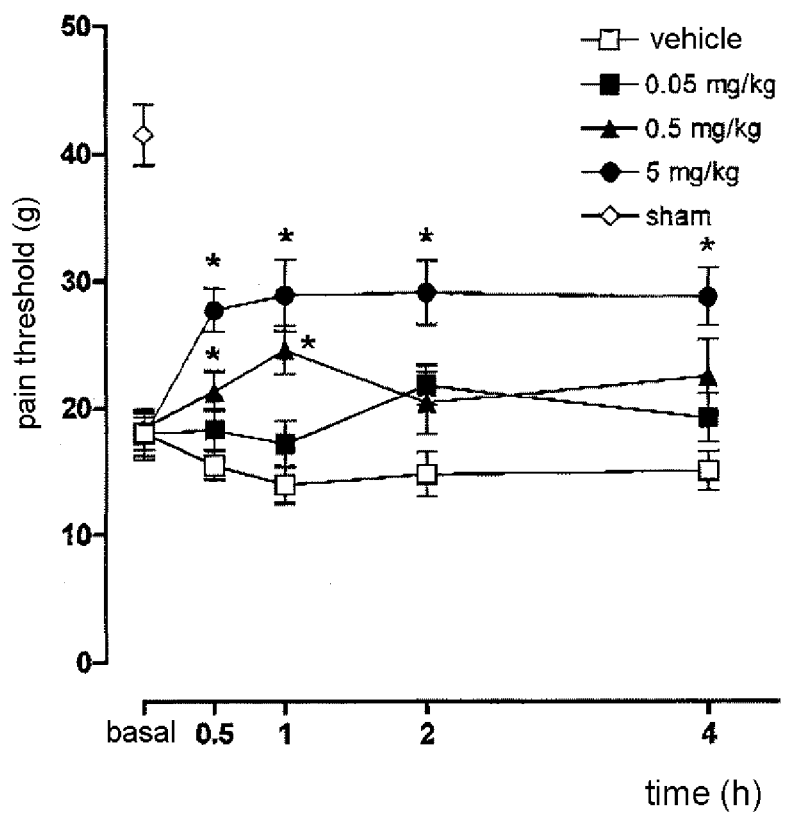
Used 7-9 rats/group
*p<0.05 vs vehicle; ANOVA followed by Dunnett test

COMPOUND WITH SEROTONINERGIC ACTIVITY, PROCESS FOR PREPARING IT AND PHARMACEUTICAL COMPOSITION COMPRISING IT

CROSS REFERENCES TO RELATED APPLICATIONS

This application is a 371 of International Patent Application No. PCT/EP09/59216, filed on Jul. 17, 2009, and claims priority to European Patent Application No. 08425516.5, filed on Jul. 29, 2008.

FIELD OF THE INVENTION

The present invention relates to a novel 2H-pyrrolo[3,4-c]quinoline compound, to a process for preparing it, to its pharmaceutical use and to a pharmaceutical composition comprising it. The invention also relates to the use of a novel 2H-pyrrolo[3,4-c]quinoline compound for preparing a pharmaceutical composition that is active in the treatment of disturbances of the serotoninergic system.

PRIOR ART

Among the many known classes of serotonin receptor, the $5HT_4$ receptors have been detected in the urinary bladder, in the gastrointestinal system, in smooth muscle and heart muscle and in specific regions of the central nervous system (Eglen R M et al., Central 5-HT4 receptors. Trends Pharmacol. Sci. 1995; 16(11): 391-8; Hedge S S and Eglen R M, Peripheral 5-HT4 receptors. FASEB J. 1996; 10(12): 1398-407). Compounds with agonist, partial agonist and antagonist activity with respect to the $5-HT_4$ receptors are potentially advantageous in the pharmacological treatment of intestinal motility disorders, and disorders of the central nervous system, of urinary incontinence and of cardiac arrhythmia (Bockaert J. et al., 5-HT4 receptors. Curr. Drug Targets—CNS Neurol. Disord. 2004, 3(1): 39-51; Gershon M D. Review article: serotonin receptors and transporters—roles in normal and abnormal gastrointestinal motility. Aliment Pharmacol. Ther. 2004; 20 (Suppl. 7): 3-14).

It is also known that certain drugs that are active on the serotoninergic system are capable of controlling chronic pain and in particular neuropathic pain.

Chronic pain represents a series of pathologies from which, on average, about 10-20% of the adult population suffers. Chronic pain is generally associated with clinical conditions characterized by chronic and/or degenerative lesions.

Chronic pain differs from acute pain mainly by the duration. Acute pain has a duration of a few days or weeks, correlated with recovery from the event that caused the pain (trauma, burns, intense efforts, surgical or dental interventions, and the like). On the other hand, chronic pain persists for months and even years, causing muscular tension, limited mobility, fatigue, loss of appetite and apathy. Chronic pain may also be manifested in a recurrent manner, with intervals of weeks, months or even years, or may be associated with chronic pathologies. Typical examples of pathologies characterized by chronic pain are rheumatoid arthritis, osteoarthritis, fibromyalgia, neuropathies, etc. [Ashburn M A, Staats P S. Management of chronic pain. Lancet 1999; 353: 1865-69].

Chronic pain, and in particular neuropathic pain, is often debilitating and is a cause of loss of working capacity and of poor quality of life. Economic and social damage thus also follow.

The analgesic drugs currently used in the treatment of neuropathic pain include non-steroidal anti-inflammatory drugs (NSAID), anti-depressants, opioid analgesics, and anti-convulsants [Woolf C J, Mannion R J, Neuropathic pain: aetiology, symptoms, mechanism, and management. Lancet 1999; 353: 1959-1964].

However, chronic pain, and in particular neuropathic pain, is notoriously difficult to treat with the drugs currently available. Consequently, the development of novel drugs has always been one of the main objectives of the pharmaceutical industry.

In addition, despite the numerous research efforts directed towards identifying a suitable analgesic compound, there are a significant number of patients whose pain condition still lacks a suitable treatment [Scholz J, Woolf C J. Can we conquer pain? Nat. Neusci. 2002; 5: 1062-76].

Patent applications WO 2004/101 548 and WO 2005/013 989 relate to the use of indazole compounds for preparing a pharmaceutical composition that is active in the treatment of neuropathic pain.

A number of compounds that are active on the serotoninergic system, in particular as $5HT_4$ receptor antagonists, were considered as being capable of having analgesic activity.

The compounds that are active on the serotoninergic system have a number of adverse effects and side effects due to their low selectivity with respect to the various serotoninergic receptors. Specifically, it is known that the general category of serotoninergic receptors is subdivided into various sub-types, for instance $5HT_{1(A-F)}$, $5HT_{2(A-C)}$, $5HT_3$, $5HT_4$, $5HT_6$ or $5HT_7$, which are variously located in diverse systems, for instance in the central and/or peripheral nervous system, in the digestive system and in the cardiovascular system. The effects of the interaction of active compounds with the serotoninergic receptors differ according to the location of these receptors.

The low selectivity often forces an interruption of or the avoidance of treatment in the case of particular types of patients who, besides the presence of chronic pain, present concomitant pathologies in specific systems, such as the cardiovascular system.

Specifically, interaction with the serotoninergic system, and even more particularly with specific sub-receptors such as $5HT_{2A}$, may give rise to adverse events in the cardiovascular system, inducing effects on the heart rhythm.

Pyrroloquinoline compounds are generally known. These compounds include in their chemical formula a pyrrole fused with a quinoline to give a tricyclic system. Depending on the position of fusion, various classes of pyrroloquinolines may be distinguished.

2H-Pyrrolo[3,4-b]quinoline compounds were described in patent application JP 2005/306 774 as pharmaceutical substances with antibacterial activity.

Pyrrolo[3,4-b]quinoline compounds were described in U.S. Pat. No. 6,335,346 as pharmaceutical substances with a sedative or hypnotic effect.

Pyrrolo[3,2-c]quinoline compounds were described in international patent application WO 98/05660 as substances capable of acting as kynurenine-3-hydroxylase (KYN-OH) inhibitors that are potentially useful in the prevention and/or treatment of neurodegenerative disturbances, for instance cerebral ischaemia and/or hypoxia, Parkinson's disease, epilepsy, Huntington's disease, Alzheimer's disease and the like.

Pyrrolo[3,2-c]quinoline compounds were also described in international patent application WO 99/09029 as substances capable of inhibiting the secretion of gastric acid, which are potentially useful for treating gastric ulcers.

Hexahydro-2H-pyrrolo[3,4-c]quinoline compounds were described in U.S. Pat. No. 4,268,513, U.S. Pat. Nos. 4,350,814 and 4,440,768 as pharmaceutical substances with antipsychotic, analgesic and antidepressant activities.

Pyrrolo[3,4-c]quinolin-1-one compounds were described in U.S. Pat. Nos. 6,323,216 and 6,413,978 as pharmaceutical substances with $5HT_3$ serotoninergic receptor antagonist activity that are potentially useful as antiemetic and antitussive agents and in various central nervous system pathologies, for instance anxiety, depression, schizophrenia, psychosis, Alzheimer's dementia and senile dementia.

5H-Pyrrolo[3,4-c]quinoline compounds were described in U.S. Pat. No. 5,908,932 as pharmaceutical substances with agonist, antagonist and inverse agonist activity on the cerebral GABA (γ-aminobutyric acid) receptors and potentially useful in the treatment of sleep disorders, anxiety and convulsions, in the treatment of benzodiazepine overdoses, and for improving attention.

DESCRIPTION OF THE INVENTION

The Applicant has found, surprisingly, that novel 2H-pyrrolo[3,4-c]quinoline compounds are capable of interacting with the serotoninergic system, with high affinity towards the $5HT_4$ serotoninergic receptor.

In addition, the Applicant has also found, surprisingly, that these novel compounds have little or no affinity for the $5-HT_{2A}$ receptor, and thus minimal adverse effects on the cardiovascular system.

Thus, the present invention relates to a compound of formula (I):

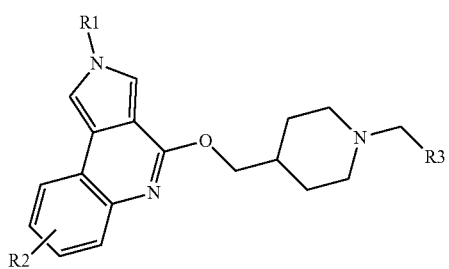

in which:

R1 is a hydrogen atom, a linear or branched alkyl group, preferably containing 1-6 carbon atoms, optionally substituted with 1 to 3 hydroxyl groups, or an alkylalkoxy group, preferably with 1-6 carbon atoms;

R2 is a hydrogen atom, a halogen atom or a linear or branched alkyl group, preferably containing 1-3 carbon atoms, —$CF_3$, —$OSO_2CF_3$, —$SO_2CH_3$, —$SO_2NHCH_3$ or —$NHSO_2CH_3$;

R3 is (i) a hydrogen atom; (ii) a linear or branched alkyl group, preferably containing 1-6 carbon atoms; (iii) an alkylalkoxy group, preferably containing 1-6 carbon atoms; (iv) an arylalkyl group or a heteroarylalkyl group, in which the alkyl group preferably contains 1-3 carbon atoms, and the aryl or heteroaryl group may be substituted with one or two substituents, which may be identical or different, chosen from a halogen atom, an alkyl group containing 1-3 carbon atoms, an alkoxy group containing 1-3 carbon atoms, a hydroxyalkyl group containing 1-3 carbon atoms, —OH, —$NR'R''$, —$NO_2$, —$CF_3$, —$CO_2R'$, R'CON(R'')—, R'$SO_2$N(R'')— and R'R''$NSO_2$—, in which R' and R'', which may be identical or different, are a hydrogen atom or an alkyl group containing 1-3 carbon atoms; (v) $R^{iv}R^vNCO(CH_2)_n$—, in which n is an integer from 0 to 2, and $R^{iv}$ and $R^v$, which may be identical or different, are a hydrogen atom, an alkyl group containing 1-3 carbon atoms, an aryl group or a heteroaryl group, optionally substituted with one or two substituents, which may be identical or different, chosen from a halogen atom, an alkyl group containing 1-3 carbon atoms, an alkoxy group containing 1-3 carbon atoms, a hydroxyalkyl group containing 1-3 carbon atoms, —OH, —$NO_2$, —$NH_2$, —$CF_3$, —$CO_2H$, —$CO_2$—$C_{1-3}$alkyl, —$SO_2NH_2$ and —$NHSO_2$—$C_{1-3}$alkyl; and (vi) $C_\gamma$—$(CH_2)_m$—, in which m is an integer from 0 to 2, and $C_\gamma$ is an alicyclic group of 3 to 7 carbon atoms or a saturated 5- or 6-membered heterocyclic group comprising at least one heteroatom chosen from N and O, optionally N-substituted with an alkyl group containing 1 to 3 carbon atoms, the acid-addition salts thereof with a pharmaceutically acceptable organic or mineral acid, and the base-addition salts thereof with a pharmaceutically acceptable organic or mineral base.

The capacity to interact with the serotoninergic system, and in particular with the $5HT_4$ serotoninergic receptor, makes these compounds particularly useful in the treatment of pathologies involving this receptor, and potentially advantageous in the pharmacological treatment of intestinal motility disorders, and disorders of the central nervous system, of urinary incontinence and of cardiac arrhythmia. In particular, the Applicant has observed that the compounds of the present invention are particularly useful in the treatment of chronic pain, and in particular of neuropathic pain.

The high selectivity towards other serotoninergic receptors, in particular the $5HT_{2A}$ receptors, reduces the adverse effects on the cardiovascular system encountered in the case of other drugs that are active on the serotoninergic system.

The compounds of the present invention are thus useful as pharmaceutical active principles, in particular for intestinal motility disorders, and disorders of the central nervous system, of urinary incontinence and of cardiac arrhythmia, preferably chronic pain, and more preferably neuropathic pain.

Thus, in a second aspect, the present invention relates to a pharmaceutical formulation comprising an effective amount of a compound of formula (I):

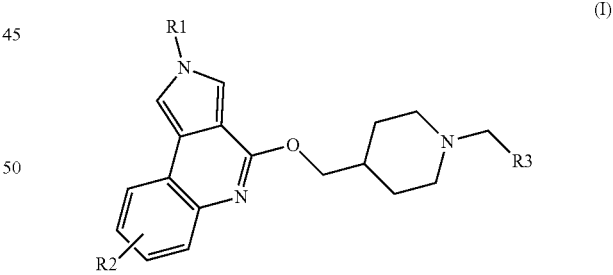

in which R1, R2 and R3 are as described above, the acid-addition salts thereof with a pharmaceutically acceptable organic or mineral acid, and the base-addition salts thereof with a pharmaceutically acceptable organic or mineral base, and at least one pharmaceutically acceptable excipient.

According to another aspect, the present invention relates to a compound of formula (I) as described previously, and pharmaceutically acceptable acid-addition or base-addition salts thereof, for pharmaceutical use.

According to a further aspect, the present invention relates to a compound of formula (I) as described previously, and pharmaceutically acceptable acid-addition or base-addition salts thereof, for the preparation of a pharmaceutical composition that is active in the treatment of intestinal motility disorders, and disorders of the central nervous system, of urinary incontinence and of cardiac arrhythmia.

In a further preferred aspect, the present invention relates to the use of a compound of formula (I) as described previously, and pharmaceutically acceptable acid-addition or base-addition salts thereof, for the preparation of a pharmaceutical composition that is active in the treatment of chronic pain, in particular neuropathic pain.

Typical examples of pathologies characterized by neuropathic pain are diabetes, cancer, immunodeficiency, traumas, ischaemia, multiple sclerosis, sciatica, trigeminal neuralgia, and post-herpetic syndrome.

Advantageously, R1 is a hydrogen atom or a linear or branched alkyl group preferably containing 1-6 carbon atoms. More preferably, R1 is a linear or branched alkyl group preferably containing 1-6 carbon atoms. Advantageously, R1 is a linear or branched alkyl group comprising from 1 to 3 OH groups.

Preferably, R2 is a hydrogen atom, a halogen atom, —$CF_3$, —$OSO_2CF_3$, —$SO_2CH_3$, —$SO_2NHCH_3$ or —$NHSO_2CH_3$. More preferably, R2 is a hydrogen atom, —$CF_3$, —$OSO_2CF_3$, —$SO_2CH_3$, —$SO_2NHCH_3$ or —$NHSO_2CH_3$.

Advantageously, R3 is chosen from the group comprising (i) a hydrogen atom; (ii) a linear or branched alkyl group, preferably containing 1-6 carbon atoms; (iii) an arylalkyl group or a heteroarylalkyl group, in which the aryl or heteroaryl group may be substituted with one or two substituents, which may be identical or different, chosen from a halogen atom, an alkyl group containing 1-3 carbon atoms, an alkoxy group containing 1-3 carbon atoms, a hydroxyalkyl group containing 1-3 carbon atoms, —OH, —NR'R", —$NO_2$, —$CO_2R'$, R'CON(R")—, R'$SO_2$N(R")— and R'R"$NSO_2$—, in which R' and R", which may be identical or different, are a hydrogen atom or an alkyl group containing 1-3 carbon atoms; (iv) $R^{iv}R^vNCO(CH_2)_n$—, in which n is an integer from 0 to 2, and $R^{iv}$ and $R^v$, which may be identical or different, are a hydrogen atom, an aryl group or a heteroaryl group; and (v) $C_\gamma$—$(CH_2)_m$—, in which m is an integer from 0 to 2, and $C_\gamma$ is a saturated heterocyclic group chosen from the group comprising morpholine, piperidine, N-methylpiperazine and pyrrolidine.

Even more advantageously, R3 is chosen from the group comprising (i) a linear or branched alkyl group containing 1-6 carbon atoms; (ii) an arylalkyl group, in which the aryl group may be substituted with a substituent chosen from an alkoxy group containing 1-3 carbon atoms, a hydroxyalkyl group containing 1-3 carbon atoms, —NR'R", —$CO_2R'$, R'CON(R")—, R'$SO_2$N(R")— and R'R"$NSO_2$—, in which R' and R", which may be identical or different, are a hydrogen atom or an alkyl group containing 1-3 carbon atoms; (iii) $R^{iv}R^vNCO(CH_2)_n$—, in which n is an integer from 0 to 2, and $R^{iv}$ and $R^v$, which may be identical or different, are a hydrogen atom or an aryl group; and (iv) $C_\gamma$—$(CH_2)_m$—, in which m is an integer from 0 to 2, and $C_\gamma$ is a morpholine or piperidine residue.

The aryl or heteroaryl group forming part of the arylalkyl or heteroarylalkyl group, which may be represented by the group R3 as described above, may be a group derived from benzene, naphthalene, pyridine, quinoline, isoquinoline, pyrazine, quinoxaline, pyrimidine, quinazoline, pyridazine, cinnoline, furan, benzofuran, isobenzofuran, pyrrole, indole, isoindole, thiophene, benzothiophene, isobenzothiophene, imidazole, benzimidazole, pyrazole, indazole, oxazole, benzoxazole, isoxazole, benzisoxazole, thiazole and benzothiazole; preferably benzene, pyridine, furan, benzofuran and pyrrole.

Typical examples of optionally substituted arylalkyl or heteroarylalkyl groups, which may be represented by the group R3 described above, are illustrated hereinbelow:

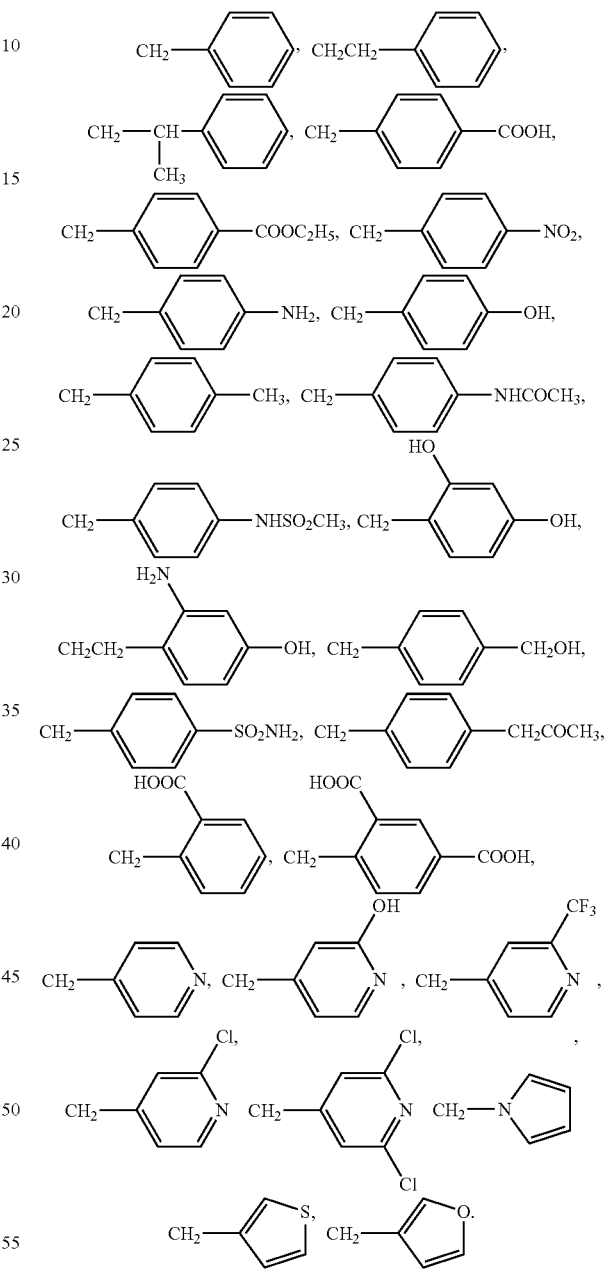

Typical examples of compounds represented by the above-mentioned formula (I) are illustrated in Table 1 below.

TABLE 1

| Compound | R1 | R2 | R3 |
|---|---|---|---|
| 1 | H | Cl | $CH_3$ |
| 2 | $C_2H_5$ | $CH_3$ | $C_2H_5$ |
| 3 | $CH_3$ | H | $CH_2CH_2CH_3$ |

TABLE 1-continued

| Compound | R1 | R2 | R3 |
|---|---|---|---|
| 4 | CH$_3$ | H | CH$_2$—C$_6$H$_5$ |
| 5 | CH(CH$_3$)$_2$ | H | CH$_2$—C$_6$H$_5$ |
| 6 | CH$_3$ | H | CONH—C$_6$H$_5$ |
| 7 | CH$_3$ | H | C$_6$H$_5$ |
| 9 | CH$_3$ | H | CH$_2$—N-morpholine |
| 10 | CH$_3$ | H | CH$_2$—C$_6$H$_4$-(4-NO$_2$) |
| 11 | CH$_3$ | H | CH$_2$—C$_6$H$_4$-(4-NH$_2$) |
| 12 | CH$_3$ | H | CH$_2$—C$_6$H$_4$-(4-COOC$_2$H$_5$) |
| 12a | CH$_3$ | H | CH$_2$—C$_6$H$_4$-(4-COOH) |
| 13 | CH$_3$ | H | CH$_2$—C$_6$H$_4$-(4-NHCOCH$_3$) |
| 14 | CH$_3$ | H | CH$_2$—C$_6$H$_4$-(4-NHSO$_2$CH$_3$) |
| 15 | CH$_3$ | H | CH$_2$—C$_6$H$_4$-(4-CH$_2$OH) |
| 16 | CH$_3$ | H | CH$_2$—C$_6$H$_4$-(4-CH$_2$COCH$_3$) |
| 17 | CH$_3$ | H | CH$_2$—C$_6$H$_4$-(2-COOCH$_3$) |
| 17a | CH$_3$ | H | CH$_2$—C$_6$H$_4$-(2-COOH) |
| 18 | CH$_3$ | H | CH$_2$—C$_6$H$_4$-(4-SO$_2$NH$_2$) |
| 19 | C$_2$H$_5$ | H | CH$_2$—C$_6$H$_4$-(4-SO$_2$NHCH$_3$) |
| 20 | CH$_2$OCH$_3$ | Br | CH$_2$—N-pyrrolo-(3-OH) |
| 21 | CH$_3$ | Cl | CONH—C$_6$H$_4$-(4-NH$_2$) |
| 22 | CH$_2$OC$_2$H$_5$ | C$_2$H$_5$ | CH$_2$—N-piperidine |
| 23 | CH$_3$ | H | CH$_2$—C$_6$H$_{11}$ |
| 24 | CH$_3$ | H | CH$_2$—C$_5$H$_9$ |

Typical examples of pharmaceutically acceptable mineral acids are: hydrochloric acid, hydrobromic acid, phosphoric acid, sulfuric acid and nitric acid. Typical examples of pharmaceutically acceptable organic acids are: acetic acid, ascorbic acid, oxalic acid, succinic acid, maleic acid, fumaric acid, tartaric acid, methanesulfonic acid, para-toluenesulfonic acid, citric acid, lactic acid, tannic acid and benzoic acid. Amino acids such as aspartic acid and glutamic acid may also be used as organic acids.

Typical examples of pharmaceutically acceptable organic and mineral bases are: mono-, di- and trialkylamines, for instance methyl-amine, dimethylamine, trimethylamine, ethylamine, diethylamine, triethylamine, propylamine, dipropylamine, tripropylamine, ethylene-diamine, mono-, di- and trialkanolamines, for instance monoethanol-amine, diethanolamine and triethanolamine; guanidine, morpholine, piperidine, pyrrolidine, piperazine, 1-butylpiperidine, 1-ethyl-2-methyl-piperidine, N-methylpiperazine, 1,4-dimethylpiperazine, N-benzylphenyl-ethylamine, N-methylglucosamine, tris(hydroxymethyl)aminomethane, ammonia, sodium hydroxide, calcium hydroxide, potassium hydroxide, aluminium hydroxide, iron hydroxide, magnesium hydroxide and zinc hydroxide. Amino acids such as arginine and lysine may also be used as organic bases.

The compounds of formula (I) described previously may be prepared according to Scheme A below, starting from novel intermediates of formula (II) by reaction with the appropriate halo derivative (III):

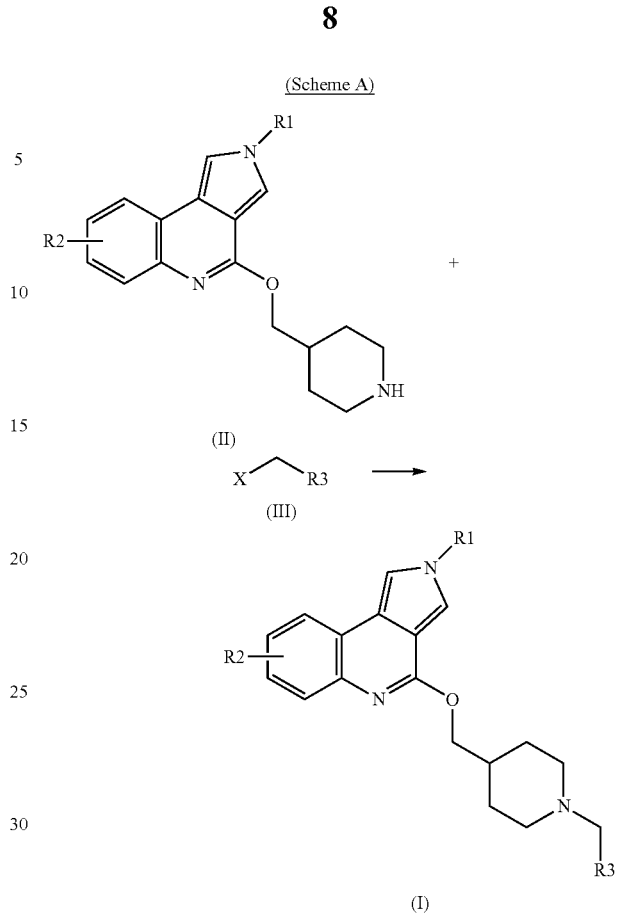

(Scheme A)

in which R1, R2 and R3 have the meaning indicated previously, and X represents a halogen atom, preferably chlorine or bromine.

The reaction of Scheme A is preferably performed in the presence of an organic or mineral basic compound and in an organic solvent.

Useful examples of organic basic substances are aliphatic or aromatic amines such as mono-, di- or trialkylamines, mono-, di- or trialkanolamines, benzylamine, N-methylbenzylamine, and the like. Useful examples of mineral bases are strong bases such as NaOH or KOH, or weak bases such as NH$_4$OH, Na$_2$CO$_3$, K$_2$CO$_3$, NaHCO$_3$, and the like.

Useful examples of organic solvents are dipolar protic and aprotic organic solvents. Typical examples of dipolar protic organic solvents are methanol, ethanol, propanol or butanol. Typical examples of dipolar aprotic organic solvents are ketones (for example acetone or methyl ethyl ketone), tetrahydrofuran, dimethylformamide, dimethyl sulfoxide, dioxane, acetonitrile, and the like.

Advantageously, the reaction is performed with heating, preferably at the boiling point of the reaction solution.

Advantageously, the reaction is performed in the presence of an activating agent, for instance potassium iodide, sodium iodide, caesium iodide, tetrabutylammonium iodide or trimethylphenylammonium iodide.

The novel intermediate compounds of formula (II) constitute a further aspect of the present invention. The novel intermediates of formula (II) may be prepared according to Scheme A1 below:

(Scheme A1)

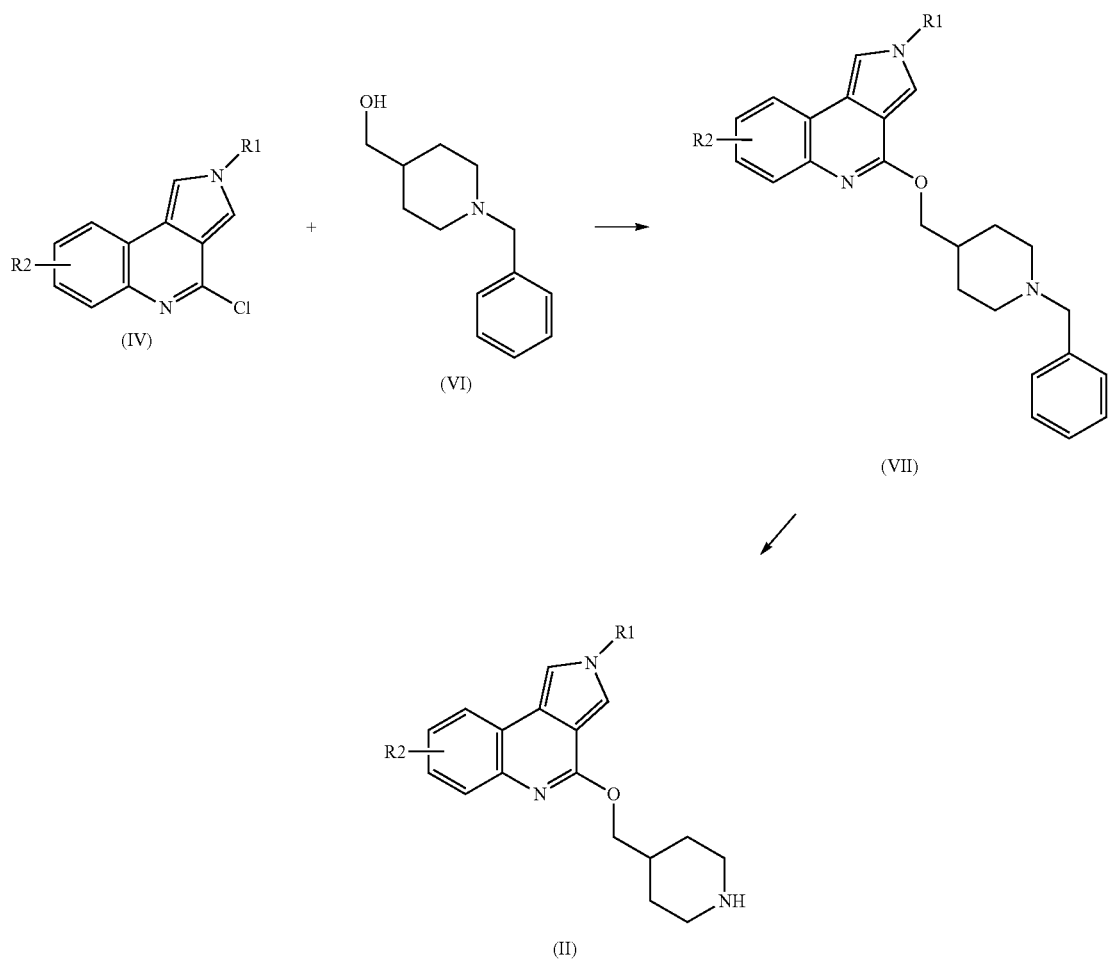

The preparation of the novel intermediates of formula (II) first involves a reaction between the 4-chloro-2H-pyrrolo[3,4-c]quinoline compound (IV) with (1-benzylpiperid-4-yl) methanol (VI), followed by a debenzylation reaction of the piperidine nitrogen via hydrogenation.

The reaction of the 4-chloro-2H-pyrrolo[3,4-c]quinoline (IV) is preferably performed with the sodium salt of (1-benzylpiperid-4-yl)methanol (VI), which is prepared by reacting compound (VI) with a strong base, for instance sodium hydride. The reaction preferably takes place in the presence of an dipolar aprotic solvent chosen from those described previously, preferably dimethylformamide. The reaction is performed with heating, preferably at reflux.

The debenzylation reaction is preferably performed by catalytic hydrogenation under a hydrogen atmosphere, preferably using as catalyst palladium-on-charcoal in an alcoholic solvent. A typical example of an alcoholic solvent is methanol. The reaction is advantageously performed at room temperature.

Alternatively, the compounds of formula (I) described previously may be prepared according to Scheme B below:

(Scheme B)

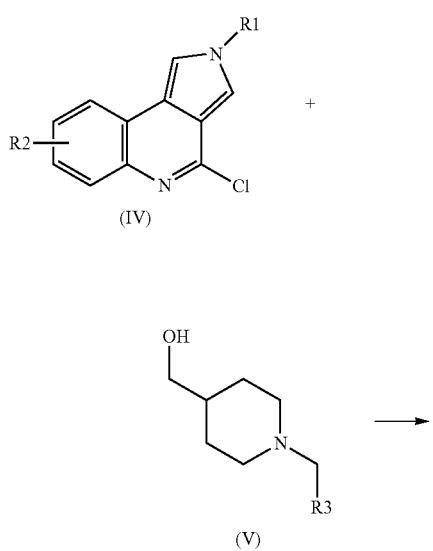

-continued

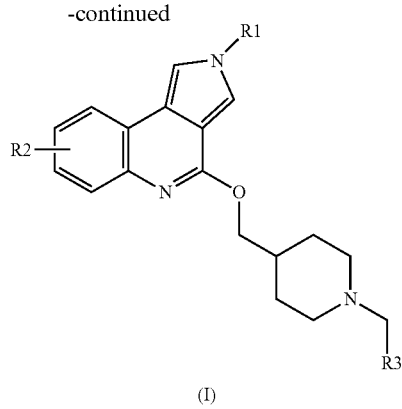

(I)

The reaction of Scheme B is preferably performed in the presence of an organic solvent, using the sodium salt of compound (V), which is prepared by reacting compound (VI) with a strong base, for instance sodium hydride.

Useful examples of organic solvents are dipolar aprotic organic solvents. Typical examples of dipolar aprotic organic solvents are those described previously, and preferably N,N-dimethylformamide and methyl ethyl ketone.

The intermediates of structure (IV) are known and their preparation is described in ARKIVOC (2004) number V, 181-195.

Preferably, the pharmaceutical compositions of the present invention are prepared in the form of suitable dosage forms including an effective dose of at least one compound of formula (I) or an acid-addition salt thereof with a pharmaceutically acceptable organic or mineral acid, or a base-addition salt thereof with a pharmaceutically acceptable organic or mineral base, and at least one pharmaceutically acceptable excipient.

The term "pharmaceutically acceptable excipient" is intended to mean, without any particular limitations, a material that is suitable for preparing a pharmaceutical composition to be administered to a living being.

These materials, known in the art, are, for example, release agents, binders, disintegrants, fillers, diluents, dyes, fluidizers, glidants, lubricants, preserving agents, stabilizers, humectants, absorbents, surfactants, buffers, salts for regulating the osmotic pressure, emulsifiers, flavourings and sweeteners.

Useful examples of pharmaceutically acceptable excipients are sugars, such as lactose, glucose or sucrose, starches, such as corn starch and potato starch, cellulose and derivatives thereof, such as sodium carboxymethylcellulose, ethylcellulose and cellulose acetate, gum tragacanth, malt, gelatin, talc, cocoa butter, waxes, oils, such as groundnut oil, cottonseed oil, safflower oil, sesame oil, olive oil, corn oil and soybean oil, glycols, such as propylene glycol, polyols, such as glycerol, sorbitol, mannitol and polyethylene glycol, esters, such as ethyl oleate and ethyl laurate, agar agar, buffers, such as magnesium hydroxide and aluminium hydroxide, alginic acid, water, isotonic solutions, ethanol, buffer solutions, polyesters, polycarbonates, polyanhydrides, and the like.

Examples of suitable dosage forms are tablets, capsules, coated tablets, granules, solutions and syrups for oral administration; antiseptic plasters, solutions, pastes, creams and ointments for transdermal administration; suppositories for rectal administration and sterile solutions for injection or aerosol administration.

Other suitable dosage forms are sustained-release forms or liposome-based forms, for either the oral or injection route.

When required for particular therapies, the pharmaceutical composition of the present invention may contain other pharmacologically active ingredients whose simultaneous administration is useful.

The amount of compound of formula (I) or of acid-addition salt or base-addition salt thereof in the pharmaceutical composition of the present invention may vary within a wide range as a function of known factors, for instance the type of pathology with which the neuropathic pain to be treated is associated, the severity of the affliction, the weight of the patient, the dosage form, the selected route of administration, the number of daily administrations and the efficacy of the selected compound of formula (I). However, the optimum amount may be readily and routinely determined by a person skilled in the art.

Typically, the amount of compound of formula (I) or of acid-addition salt or base-addition salt thereof in the pharmaceutical composition of the present invention will be such that it ensures a level of administration of between 0.001 and 100 mg/kg/day of compound of formula (I), expressed as non-salified free compound. Preferably, the level of administration will be between 0.05 and 50 mg/kg/day and even more preferably between 0.1 and 10 mg/kg/day.

The dosage forms of the pharmaceutical composition of the present invention may be prepared according to techniques well known to pharmaceutical chemists, including mixing, granulation, compression, dissolution, sterilization and the like.

The activity in the treatment of chronic pain of the compounds of formula (I) was demonstrated by means of an experimental model in rats represented by the allodynia induced by ligature of the sciatic nerve.

As is known to those skilled in the art, the abovementioned experimental model may be considered as predictive of activity in man.

The experimental model of ligature of the sciatic nerve in rats represents a neuropathy that reproduces a series of responses similar to those observed in man in numerous traumatic and pathological conditions associated with neuropathic pain. The reason for this is that ligature of the sciatic nerve is capable of inducing a syndrome associated with the activation of specific circuits dedicated to controlling the perception of pain and characterized by the appearance of allodynia, hyperalgia and spontaneous pain. This model is well known to constitute a valid instrument for studying drugs to be used in the treatment of neuropathic pain in man, and in particular in controlling conditions such as allodynia and hyperalgia.

Typical examples of human pathologies characterized by the dysfunctions described in the abovementioned experimental model and characterized by the presence of neuropathic pain are diabetes, cancer, immunodeficiency, trauma, ischemia, multiple sclerosis, sciatica, trigeminal neuralgia and post-herpetic syndrome.

Confirmation of the binding to the serotoninergic receptors was performed by means of a biochemical test on purified membranes from recombinant human cells that stably express the specific receptors or from selected animal tissues as described in particular in Grossman C. J. et al. (1993), Br. J. Pharmacol. 109: 618-624, Bonhaus D. W. et al. (1995), Br. J. Pharmacol. 115(4): 622-628; and Saucier C. et al. (1997), J. Neurochem. 68(5): 1998-2011.

As is known to those skilled in the art, this test constitutes a predictive model of molecular interaction and of selectivity with the selected receptors.

Tests

1. Allodynia Induced by Ligature of the Sciatic Nerve in Rats

Male CD rats weighing 200-250 g on arrival were used.

The allodynia was induced by ligature under anaesthesia of the sciatic nerve of the left hindleg [Seltzer Z, Dubner R, Shir Y. A novel behavioral model of neuropathic pain disorders produced in rats by partial sciatic nerve injury. Pain 1990; 43: 205-218; Bennet G J, Xie Y K. A peripheral mononeuropathy in rat that produces disorders of pain sensation like those seen in man. Pain 1988; 33: 87-107]. At least two weeks after ligature of the sciatic nerve, rats that showed a reduction of at least 50% in the response threshold recorded before the intervention were selected. The pain threshold was measured with a von Frey machine, which makes it possible, by applying a gradual increase in pressure to the paw of the left hindleg of the rat, to record the nociceptive response, expressed in grams, corresponding to the moment at which the animal withdraws the leg.

At 30 minutes, 1, 2 and 4 hours of treatment, the pain threshold measured in control animals was compared with that measured in animals treated with the test product (compound 12a of Table 1).

The control animals were treated with the same vehicle (methylcellulose) used to administer the test product. The results are illustrated in FIG. 1.

2. Binding to the Serotoninergic Receptors

Confirmation of the binding to the serotoninergic receptors was made using purified membranes from selected animal tissues or from recombinant human cells that stably express the specific receptors.

Binding to the $5-HT_4$ serotonin receptor was performed using standard methods described in: Grossman C. J., Kilpatrick G. J. and Bunce K. T. (1993) "Development of a radioligand binding assay for $5-HT_4$ receptors in guinea-pig and rat brain." Br. J. Pharmacol. 109: 618-624. The starting materials used were an homogenate of guinea pig striatum and RS-23597190 as reference compound. The test compounds were tested at six concentrations to obtain the pKi values of the individual compounds.

Binding to the human $5-HT_{2A}$ serotonin receptor was performed via the standard method described in Bonhaus, D. W., Bach C., De Souza A., Salazar F. H., Matsuoka B. D., Zuppan P., Chan H. W., Eglen R. M. (1995): "The pharmacology and distribution of human 5-hydroxytryptamine 2B ($5-HT_{2B}$) receptor gene products: comparison with $5-HT_{2A}$ and $5-HT_{2C}$ receptors." Br. J. Pharmacol. 115(4): 622-628; and Saucier C., Albert P. R. (1997): "Identification of an endogenous 5-hydroxytryptamine 2A receptor in NIH-3T3 cells: agonist-induced down-regulation involves decreases in receptor RNA and number." J. Neurochem. 68(5): 1998-2011. The test compounds were tested at six concentrations to obtain the pKi values of the individual compounds.

The values of affinity for the $5-HT_4$ and $5-HT_{2A}$ receptor of a number of compounds of formula (I) according to the present invention are given, respectively, in Tables 2 and 3, and expressed as pKi, the value of which is proportionately greater the greater the affinity of the compound for the receptor.

TABLE 2

| Compound | $5-HT_4$ (pKi) |
|---|---|
| 3 | 7.83 |
| 4 | 8.73 |
| 5 | 6.86 |
| 6 | 6.88 |
| 9a | 8.64 |
| 11a | 8.34 |
| 12a | 8.65 |
| 13 | 8.73 |
| 15 | 8.00 |
| 16 | 7.72 |

TABLE 3

| Compound | $5-HT_2$ (pKi) |
|---|---|
| 3 | <6 |
| 9a | <5 |
| 11a | 6.6 |
| 12a | <5 |
| 13 | <6 |

The data of Tables 2 and 3 demonstrate that the indicated compounds of formula (I) show high affinity for the $5-HT_4$ receptor, but little or no affinity for the $5-HT_{2A}$ receptor.

SYNTHETIC EXAMPLES

1a) Ethyl 3-(2-nitrophenyl)propanoate

A solution of 2-nitrobenzaldehyde (132 mmol; 20.0 g) in absolute ethanol (220 ml) was added to a mixture of triethylphosphonium acetate (159 mmol; 35.7 g; 31.9 ml) and anhydrous potassium carbonate (397 mmol; 54.9 g). The mixture was refluxed with vigorous stirring for 1 hour 30 minutes. After cooling, the ethanol was removed under reduced pressure, water (500 ml) was added and the resulting solution was extracted with ethyl acetate (3×300 ml). The combined organic phases were washed with saturated NaCl solution (3×300 ml), dried over anhydrous sodium sulfate and evaporated under reduced pressure. The crude product obtained was purified on a column of alumina (eluting with chloroform) to give 27.6 g (94%) of final product:

yellow oil, $^1H$ NMR (CDCl$_3$, δ ppm): 1.37 (t, 3H); 4.31 (q, 2H); 6.38 (d, 1H); 7.55-7.59 (m, 1H); 7.68 (m, 2H); 8.04-8.14 (m, 2H).

1b) Ethyl 4-(2-nitrophenyl)-1H-pyrrole-3-carboxylate

A solution of ethyl 3-(2-nitrophenyl)propanoate (120 mmol; 26.6 g) and 4-toluenesulfonylmethyl isocyanate (TosMIC) (130 mmol; 25.4 g) in a mixture of dimethyl sulfoxide and anhydrous ethyl ether (150 and 300 ml) was added dropwise to a suspension of 60% sodium hydride in paraffin (260 mmol; 10.4 g) in anhydrous ethyl ether (300 ml), under a stream of argon. After the addition, the mixture was stirred at room temperature for 25 minutes, water (500 ml) was then added and the resulting solution was extracted with ethyl acetate (3×600 ml). The combined organic phases were washed with saturated NaCl solution (3×300 ml), dried over anhydrous sodium sulfate and evaporated under reduced pressure. The crude product obtained was purified on a column of alumina (eluting with a 1/1 chloroform/ethyl acetate mixture) to give 12.8 g (41%) of final product having the following characteristics:

yellow solid, m.p. 159-161° C. (crystallization solvent: ethanol),

¹H NMR (CDCl₃, δ ppm): 2.51 (m, 3H); 4.01 (q, 2H); 6.51 (m, 1H); 7.31-7.33 (m, 2H); 7.39-7.41 (m, 2H); 7.49-7.53 (m, 1H); 7.92-7.94 (m, 1H); 12.0 (s, 1H).

1c) 2H-Pyrrolo[3,4-c]quinolin-4(5H)-one

To a solution of the compound prepared in Example 1b (7.7 mmol; 2.0 g) in glacial acetic acid (100 ml) thermostatically maintained at 85° C. was added over 15 minutes iron powder (120 mmol; 6.7 g). The mixture was left stirring at this temperature for 45 minutes. After cooling, the iron was removed by filtration and washed several times with tetrahydrofuran, and the filtrate was evaporated under reduced pressure. The crude product was chromatographed on a column of alumina (eluting with ethyl acetate) to give 1.05 g (74%) of final product having the following characteristics:
red solid, which sublimes at 280° C. (ethanol),
¹H NMR (DMSO-d6, δ ppm): 7.05-7.28 (m, 3H); 7.57-7.63 (m, 2H); 7.84-7.88 (m, 1H); 10.7 (s, 1H); 12.1 (s, 1H).

1d) 2-Methyl-2H-pyrrolo[3,4-c]quinolin-4(5H)-one

To a solution of the product prepared in Example 1c (11.0 mmol, 2.0 g) in anhydrous N,N-dimethylformamide (10 ml) were added anhydrous potassium carbonate (11.0 mmol; 1.5 g) and methyl iodide (11.0 mmol; 1.54 g; 0.68 ml). The mixture was maintained thermostatically at 90° C. and stirred overnight. After cooling, the reaction mixture was treated with water (30 ml) and filtered. The solid was dried under an infrared lamp and chromatographed on a column of silica (eluting with a 10/1 chloroform/methanol mixture) to give 0.96 g (45%) of pure product having the following characteristics:
red solid which sublimes at 225° C. (toluene),
¹H NMR (DMSO-d6, δ ppm): 3.91 (s, 3H); 7.09-7.25 (m, 3H); 7.58-7.81 (m, 3H); 10.73 (s, 1H).

1e) 4-Chloro-2-methyl-2H-pyrrolo[3,4-c]quinoline (Compound of Formula IV: R1=CH₃; R2=H)
A mixture of the product prepared in Example 1d (5.0 mmol; 1.0 g), phosphorus oxychloride (16.2 ml) and triethylamine (1.2 ml) was maintained at 120° C. for 6 hours. After cooling, the reaction mixture was poured cautiously onto ice and extracted with ethyl acetate (3×100 ml). The combined organic phases were washed with saturated NaCl solution (1×50 ml), with saturated sodium bicarbonate solution (3×50 ml) and then again with saturated NaCl solution (3×50 ml). The organic solution was dried over anhydrous sodium sulfate and evaporated under reduced pressure. The crude product obtained was purified on a column of silica (eluting with a 1/1 n-hexane/ethyl acetate mixture) to give 1.0 g (92%) of final product having the following characteristics:
yellow solid, m.p. 123-124° C. (benzene),
¹H NMR (DMSO-d6, δ ppm): 4.09 (s, 3H); 7.51-7.58 (m, 2H); 7.76 (m, 1H); 7.82-7.85 (m, 1H); 7.97 (m, 1H); 8.15-8.17 (m, 1H).

1f) 2-Isopropyl-2H-pyrrolo[3,4-c]quinolin-4(5H)-one

To a solution of the product prepared in Example 1c (16.3 mmol; 3.0 g) in dioxane (150 ml) brought to reflux was added potassium metal (14.8 mmol; 580 mg) and the mixture was stirred at reflux until total disappearance of the metal was observed (about 2 hours). After cooling, 2-iodopropanol (16.3 mmol; 2.77 g) and 18-crown-6 ether (14.8 mmol; 3.92 g) were added and the mixture was refluxed for 5 hours 30 minutes. A further portion of 2-iodopropanol (8.1 mmol; 1.38 g) was then added and the reaction mixture was stirred at reflux for a further 15 hours. After cooling, the dioxane was removed under reduced pressure and the residue was taken up in ethyl acetate (100 ml) and washed with saturated NaCl solution (3×50 ml). The organic solution was dried over anhydrous sodium sulfate and the solvent was removed under reduced pressure to obtain a crude product, which was chromatographed on a column of alumina (eluting with ethyl acetate). 0.9 g (24%) of a product having the following characteristics was obtained:
white solid, m.p. 189-190° C. (toluene),
¹H NMR (DMSO-d6, δ ppm): 1.48 (d, 6H); 4.52 (m, 1H); 7.02-7.20 (m, 3H); 7.63-7.70 (m, 2H); 7.77 (m, 1H); 10.62 (s, 1H).

1g) 4-Chloro-2-isopropyl-2H-pyrrolo[3,4-c]quinoline (Compound of formula IV: R1=CH(CH₃)₂; R2=H)
A mixture of the product prepared in Example 1f (4.4 mmol; 1.0 g), phosphorus oxychloride (14.3 ml) and triethylamine (1.1 ml) was maintained at 120° C. for 25 minutes. After cooling, the reaction mixture was poured cautiously onto ice and extracted with ethyl acetate (3×100 ml). The organic phases were combined and washed with saturated NaCl solution (1×50 ml), with saturated sodium bicarbonate solution (3×50 ml) and then again with saturated NaCl solution (3×50 ml). The organic solution was then dried over anhydrous sodium sulfate and evaporated under reduced pressure. The crude product obtained was purified on a column of silica (eluting with chloroform) to give 0.9 g (91%) of final product having the following characteristics:
yellow solid, m.p. 70-72° C. (cyclohexane),
¹H NMR (CDCl₃, δ ppm): 1.64 (d, 6H); 4.59 (m, 1H); 7.46-7.49 (m, 3H); 7.55 (m, 1H); 7.93-7.98 (m, 2H).

2a) 1-Butyl-4-piperidinemethanol (Compound of Formula V: R3=CH₂CH₂CH₃)
A mixture of ethyl isonipecotate (31.8 mmol; 5.0 g), anhydrous potassium carbonate (63.6 mmol; 8.8 g) and 1-bromobutane (31.8 mmol; 4.36 g) in absolute ethanol (63 ml) was stirred at reflux for 3 hours. After cooling, the carbonate was removed by filtration and the filtrate evaporated under reduced pressure. 7.68 g of ethyl 4-butylisonipecotate were obtained in the form of an oil, which was used for the following reaction without further purification. This product was dissolved in anhydrous ethyl ether (32 ml) and added dropwise to a suspension of lithium aluminium hydride (41.3 mmol; 1.57 g) in the same solvent (20 ml) cooled to 0° C. The reaction mixture was stirred at room temperature for 15 hours. After cooling to 0° C., ice was added cautiously and the hydroxides thus formed were removed by filtration. After separating the two phases, the ether phase was dried over anhydrous sodium sulfate and evaporated under reduced pressure to give 5.1 g (94%) of final compound as a clear oil.
¹H NMR (CDCl₃, δ ppm): 0.89 (t, 3H); 1.26-1.32 (m, 4H); 1.44-1.51 (m, 3H); 1.72 (d, 2H); 1.89-1.95 (m, 2H); 2.29-2.33 (m, 3H); 2.94-2.97 (m, 2H); 3.46 (d, 2H).

2b) Ethyl 4-(2-phenylethyl)isonipecotate

A mixture of ethyl isonipecotate (64 mmol; 10.0 g), anhydrous potassium carbonate (192 mmol; 26.5 g) and phenylethyl bromide (77 mmol, 14.25 g) in anhydrous N,N-dimethylformamide (100 ml) was stirred at 70° C. for 5 hours 30 minutes. After cooling, the reaction mixture was diluted with water (300 ml) and extracted with ethyl acetate (3×200 ml). The combined organic phases were washed with saturated NaCl solution (3×100 ml), dried over sodium sulfate and evaporated under reduced pressure. A crude product was obtained, which was purified on a column of alumina (eluting with 2/1 n-hexane/ethyl acetate) to give 14.0 g (84%) of pure product as a yellow oil.

$^1$H NMR (CDCl$_3$, δ ppm): 1.22-1.27 (t, 3H); 1.75-1.85 (m, 2H); 1.92-1.96 (m, 1H); 2.09-2.14 (t, 2H); 2.26-2.33 (m, 1H); 2.57-2.61 (m, 2H); 2.79-2.83 (m, 2H); 2.95-2.98 (m, 2H); 4.10-4.16 (q, 2H).

2c) 1-(2-Phenylethyl)-4-piperidinemethanol (Compound of formula V: R3=CH$_2$Ph)

To a suspension of lithium aluminium hydride (70 mmol; 2.66 g) in anhydrous THF (40 ml) at 0° C. was added dropwise a solution of ethyl 4-(2-phenylethyl)isonipecotate (54 mmol; 14.0 g) in the same solvent (130 ml). The reaction mixture was stirred at room temperature for 10 minutes. After cooling to 0° C., ice was added cautiously and the hydroxides thus formed were removed by filtration. After removing the THF under reduced pressure, the aqueous phase was extracted with ethyl acetate (3×100 ml). The combined organic phases were washed with saturated NaCl solution (3×100 ml), dried over sodium sulfate and evaporated under reduced pressure. A crude product was obtained, which was purified on a column of alumina (eluting with ethyl acetate) to give 7.9 g (67%) of pure product having the following characteristics:

yellow solid, m.p. 89-90° C. (cyclohexane),
$^1$H NMR (CDCl$_3$, δ ppm): 1.25-1.43 (m, 2H); 1.50-1.58 (m, 2H); 1.76-1.79 (m, 2H); 2.03-2.09 (m, 2H); 2.59-2.64 (m, 2H); 2.82-2.87 (m, 2H); 3.05-3.08 (m, 2H); 3.52 (m, 2H); 7.18-7.31 (m, 5H).

2d) 4-Piperidinemethanol

To a suspension of lithium aluminium hydride (8.3 mmol; 310 mg) in anhydrous THF (5 ml) at 0° C. was added dropwise a solution of ethyl isonipecotate (6.4 mmol; 1.0 g) in anhydrous THF (5 ml). The reaction mixture was stirred at room temperature for 35 minutes. After cooling to 0° C., aqueous ethanol (95%) was added cautiously and the hydroxides thus formed were removed by filtration. The organic phase was dried over anhydrous sodium sulfate and evaporated under reduced pressure to give 1.34 g (100%) of pure product as an oil.

$^1$H NMR (DMSO-d6, δ ppm): 1.09-1.18 (m, 2H); 1.50 (m, 1H); 1.66-1.69 (m, 2H); 2.53-2.61 (m, 3H); 3.05-3.08 (m, 2H); 3.25 (d, 2H); 4.60 (s, 1H).

2e) N-Phenyl-2-(4-hydroxymethylpiperid-1-yl)acetamide (Compound of Formula V: R3=CONHPh)

To a solution of 4-piperidinemethanol (9.65 mmol; 1.15 g) in N,N-dimethylformamide (15 ml) were added 2-chloro-N-phenylacetamide (11.6 mmol; 1.97 g) and anhydrous potassium carbonate (29 mmol; 4.0 g). The mixture was stirred at 70° C. for 2 hours 30 minutes. After cooling, the reaction mixture was diluted with water (15 ml) and extracted with ethyl acetate (3×50 ml). The combined organic phases were washed with saturated NaCl solution, dried over anhydrous sodium sulfate and evaporated under reduced pressure. The residue was chromatographed on a column of silica (eluting with a 1/1 chloroform/ethyl acetate mixture) to give 420 mg (27%) of pure product having the following characteristics:

white solid, m.p. 93-95° C. (benzene)
$^1$H NMR (CDCl$_3$, δ ppm): 1.34-1.38 (m, 2H); 1.58 (m, 1H); 1.81 (m, 2H); 2.10 (m, 1H); 2.24-2.28 (m, 2H); 2.93-2.96 (m, 2H); 3.12 (s, 2H); 3.54 (d, 2H).

2f) Ethyl 4-benzylisonipecotate

A mixture of ethyl isonipecotate (65 mmol; 10.2 g), anhydrous potassium carbonate (195 mmol; 26.9 g) and benzyl bromide (78 mmol; 13.36 g) in anhydrous N,N-dimethylformamide (100 ml) was stirred at 70° C. for 18 hours. After cooling, the reaction mixture was diluted with water (300 ml) and extracted with ethyl acetate (3×200 ml). The combined organic phases were washed with saturated NaCl solution (3×100 ml), dried over sodium sulfate and evaporated under reduced pressure. A crude product was obtained, which was purified on a column of alumina (eluting with chloroform) to give 13.84 g (86%) of pure product as a yellow oil.

$^1$H NMR (CDCl$_3$, δ ppm): 1.28-1.32 (t, 3H); 1.81 (m, 4H); 2.07-2.12 (m, 2H); 2.34 (m, 1H); 2.91 (m, 2H); 3.55 (m, 2H); 4.15-4.21 (m, 2H); 7.31-7.38 (m, 5H).

2g) (1-Benzyl-4-piperidyl)methanol (Compound VI)

To a solution of lithium aluminium hydride (72 mmol; 2.7 g) in anhydrous THF (40 ml) at 0° C. was added dropwise a solution of ethyl 4-benzylisonipecotate (55 mmol; 13.7 g) in the same solvent (130 ml). The reaction mixture was stirred at room temperature for 20 minutes. After cooling to 0° C., ice was added cautiously and the hydroxides thus formed were removed by filtration. After removing the tetrahydrofuran under reduced pressure, the aqueous phase was extracted with ethyl acetate (3×100 ml). The combined organic phases were washed with saturated NaCl solution (3×100 ml), dried over sodium sulfate and evaporated under reduced pressure. A crude product was obtained, which was purified on a column of alumina (eluting with ethyl acetate) to give 10.25 g (90.5%) of pure product as an oil.

$^1$H NMR (CDCl$_3$, δ ppm): 1.29-1.39 (m, 2H); 1.53-1.56 (m, 1H); 1.74-1.78 (m, 2H); 1.86 (s, 1H); 1.99-2.05 (m, 2H); 2.94-2.98 (m, 2H); 3.52-3.56 (m, 4H); 7.30-7.38 (m, 5H).

3) 4-[(1-Butylpiperid-4-yl)methyloxy]-2-methyl-2H-pyrrolo[3,4-c]quinoline (Compound of Formula I: R1=CH$_3$; R2=H; R3=CH$_2$CH$_2$CH$_3$)

To a suspension of 60% NaH in paraffin (6.72 mmol; 270 mg) in anhydrous N,N-dimethylformamide (14 ml) was added dropwise a solution of (1-butyl-4-piperidyl)methanol (6.72 mmol; 1.14 g) dissolved in anhydrous N,N-dimethylformamide (14 ml). The reaction mixture was stirred at room temperature for 10 minutes. The alkoxide thus formed was added dropwise to a solution of the product prepared in Example 1e (1.92 mmol; 470 mg) in anhydrous N,N-dimethylformamide (14 ml) preheated to 146° C. The reaction mixture was stirred at 146° C. for 1 hour 10 minutes. After cooling, the mixture was poured onto ice and extracted with ethyl acetate (3×50 ml). The combined organic phases were washed with saturated NaCl solution (3×20 ml), dried over anhydrous sodium sulfate and evaporated under reduced pressure. The residue was chromatographed on a column of alumina (using chloroform as eluent) to give 520 mg (71%) of pure product having the following characteristics:
solid, m.p. 83-85° C. (benzene/cyclohexane),
$^1$H NMR (CDCl$_3$, δ ppm): 0.97 (t, 3H); 1.35-1.59 (m, 6H); 1.90-2.07 (m, 5H); 2.37 (m, 2H); 3.03 (m, 2H); 3.99 (s, 3H); 4.49 (d, 2H); 7.28-7.49 (m, 4H); 7.75 (m, 1H); 7.88 (m, 1H).

4) 4-{[1-(2-Phenyl)ethylpiperidine-4-yl]methoxy}-2-methyl-2H-pyrrolo[3,4-c]quinoline (Compound of formula I: R1=CH$_3$; R2=H; R3=CH$_2$Ph)
To a suspension of 60% NaH in paraffin (8.05 mmol; 320 mg) in anhydrous N,N-dimethylformamide (16 ml) was added dropwise a solution of 1-(2-phenylethyl)-4-piperidinemethanol (8.05 mmol; 1.77 g) in anhydrous N,N-dimethylformamide (16 ml). The reaction mixture was stirred at room temperature for 10 minutes. The alkoxide thus formed was added dropwise to a solution of the product prepared in Example 1e (2.3 mmol; 500 mg) in anhydrous N,N-dimethylformamide (16 ml) preheated to 146° C. The reaction mixture was stirred at 146° C. for 7 hours 30 minutes. After cooling, the reaction mixture was poured onto ice and extracted with ethyl acetate (3×50 ml). The combined organic phases were washed with saturated NaCl solution (3×20 ml), dried over anhydrous sodium sulfate and evaporated under reduced pressure. The residue was chromatographed on a column of alumina (eluting with 4/1 n-hexane/ethyl acetate) to give 620 mg (68%) of pure product having the following characteristics:
solid, m.p. 90-92° C. (benzene/cyclohexane),
$^1$H NMR (CDCl$_3$, δ ppm): 1.67 (m, 2H); 1.94-1.97 (m, 3H); 2.17 (m, 2H); 2.69 (m, 2H); 2.90 (m, 2H); 3.15 (m, 2H); 3.98 (s, 3H); 4.49 (d, 2H); 7.20-7.42 (m, 9H); 7.74 (m, 1H); 7.88 (m, 1H).

5) 4-{[1-(2-Phenyl)ethylpiperid-4-yl]methoxy}-2-isopropyl-2H-pyrrolo[3,4-c]quinoline (Compound of formula I: R1=CH(CH$_3$)$_2$; R2=H; R3=CH$_2$Ph)
To a suspension of 60% NaH in paraffin (7.7 mmol; 310 mg) in anhydrous N,N-dimethylformamide (15 ml) was added dropwise a solution of 1-(2-phenylethyl)-4-piperidinemethanol (7.7 mmol; 1.69 g) in anhydrous N,N-dimethylformamide (15 ml). The reaction mixture was stirred at room temperature for 10 minutes. The alkoxide thus formed was added dropwise to a solution of the product prepared in Example 1g (2.2 mmol; 540 mg) in anhydrous N,N-dimethylformamide (15 ml) preheated to 146° C. The reaction mixture was stirred at 146° C. for 1 hour. After cooling, the mixture was poured onto ice and extracted with ethyl acetate (3×50 ml). The combined organic phases were washed with saturated NaCl solution (3×20 ml), dried over anhydrous sodium sulfate and evaporated under reduced pressure. The residue was chromatographed on a column of alumina (eluting with a 4/1 n-hexane/ethyl acetate mixture) to give 680 mg (73%) of pure product having the following characteristics:
solid, m.p. 90-93° C. (n-hexane),
$^1$H NMR (CDCl$_3$, δ ppm): 1.61-1.66 (m, 8H); 1.94 (m, 3H); 2.12 (m, 2H); 2.65 (m, 2H); 2.86 (m, 2H); 3.12 (m, 2H); 4.49 (d, 2H); 4.54 (m, 1H); 7.21-7.45 (m, 9H); 7.74 (m, 1H); 7.90 (m, 1H).

5a) 4-{[1-(2-Phenyl)ethylpiperid-4-yl]methoxy}-2-isopropyl-2H-pyrrolo[3,4-c]quinoline hydrochloride A solution of hydrochloric methanol was prepared by dropwise addition of acetyl chloride (2.67 mmol; 200 mg) to 10 ml of methanol cooled in an ice bath. The solution was stirred gently for a few minutes, followed by dropwise addition of a solution of the product prepared in Example 5 (2.34 mmol; 1.0 g) in methanol (5.0 ml). Once the addition was complete, the mixture was stirred at 0° C. for 45 minutes, followed by addition of anhydrous ethyl ether (about 200 ml) until precipitation of the salt was observed. The salt obtained was filtered off, washed with anhydrous ethyl ether (3×2 ml) and dried under vacuum at 45° C. for 6 hours. 630 mg (58%) of pure product having the following characteristics were obtained:
solid, m.p. 138-140° C. (isopropyl ether/isopropanol)
$^1$H NMR (DMSO-d6, δ ppm): 1.57 (d, J=6.59 Hz, 6H); 1.79-2.29 (m, 5H); 2.86-3.47 (m, 6H); 3.63 (d, J=11.71 Hz, 2H); 4.55 (d, J=4.03 Hz; 2H); 4.68 (septet, J=6.59 Hz; 1H); 7.20-7.48 (m, 7H); 7.80 (bs, 1H); 7.95-8.16 (m, 3H); 10.93 (bs, 1H).

6) N-Phenyl-2-{4-[2-methyl-2H-pyrrolo[3,4-c]quinolin-4-yloxy-methyl]piperid-1-yl}acetamide (Compound of formula I: R1=CH$_3$; R2=H; R3=CONHPh)
To a suspension of 60% NaH in paraffin (30.8 mmol; 1.23 g) in anhydrous N,N-dimethylformamide (60 ml) was added dropwise a solution of N-phenyl-2-(4-hydroxymethylpiperid-1-yl)acetamide (30.8 mmol; 7.65 g) in anhydrous N,N-dimethylformamide (60 ml). The mixture was stirred at room temperature for 10 minutes. The alkoxide thus formed was added dropwise to a solution of the product prepared in Example 1e (8.8 mmol; 1.9 g) in anhydrous N,N-dimethylformamide (60 ml) preheated to 146° C. The reaction mixture was stirred at 146° C. for 3 hours 30 minutes. After cooling, the mixture was poured onto ice and extracted with ethyl acetate (3×150 ml). The combined organic phases were washed with saturated NaCl solution (3×100 ml), dried over anhydrous sodium sulfate and evaporated under reduced pressure. The residue was chromatographed on a column of alumina (eluting with a 2/1 n-hexane/ethyl acetate mixture) to give 2.9 g (77%) of pure product as an oil.
$^1$H NMR (CDCl$_3$, δ ppm): 1.65 (m, 2H); 2.04 (m, 3H); 2.45 (m, 2H); 3.10 (m, 2H); 3.26 (s, 2H); 4.03 (s, 3H); 4.56 (d, 2H); 7.17 (t, J=7.6 Hz; 1H); 7.33-7.48 (m, 6H); 7.66 (d, J=7.6 Hz; 2H); 7.80 (m, 1H); 7.95 (m, 1H).

6a) N-Phenyl-2-{4-[2-methyl-2H-pyrrolo[3,4-c]quinolin-4-yloxy-methyl]piperid-1-yl}acetamide hydrochloride A solution of hydrochloric methanol was prepared by dropwise addition of acetyl chloride (1.32 mmol; 100 mg) to 5 ml of methanol cooled in an ice bath. The reaction mixture was stirred gently for a few minutes, followed by dropwise addition of a solution of the amine prepared in Example 6 (1.2 mmol; 500 mg) in methanol (3.5 ml). Once the addition was complete, the mixture was stirred at 0° C. for 45 minutes, followed by addition of anhydrous ethyl ether (about 100 ml) until precipitation of the salt was observed. After triturating at room temperature overnight, the salt obtained was filtered off, washed with anhydrous ethyl ether (3×2 ml) and dried under vacuum at 45° C. for 2 days. 420 mg (75%) of pure product having the following characteristics were thus obtained:
solid, m.p. 163-165° C. (methanol),
$^1$H NMR (DMSO-d6, δ ppm): 1.66-2.41 (m, 5H); 3.10-3.32 (m, 2H); 3.63 (d, J=11.39 Hz; 2H); 4.01 (s, 3H); 4.19 (d, J=3.80 Hz; 2H); 4.53 (d, J=5.61 Hz; 2H); 7.12 (t, J=7.35 Hz;

1H); 7.28-7.50 (m, 4H); 7.59-7.93 (m, 5H); 8.03 (dd, J=7.43; 1.65 Hz; 1H); 10.14 (bs, 1H); 11.02 (s, 1H).

7) 4-[(1-Benzylpiperid-4-yl)methyloxy]-2-methyl-2H-pyrrolo[3,4-c]quinoline (Compound of formula VII: R1=CH$_3$; R2=H)
(Compound of formula I: R1=CH$_3$, R2=H, R3=Ph)

To a suspension of 60% NaH in paraffin (16.1 mmol; 650 mg) in anhydrous N,N-dimethylformamide (32 ml) was added dropwise a solution of (1-benzyl-4-piperidyl)methanol (16.1 mmol; 3.32 g) in anhydrous N,N-dimethylformamide (32 ml). The mixture was stirred at room temperature for 10 minutes. The alkoxide thus formed was added dropwise to a solution of the product prepared in Example 1e (4.6 mmol; 1.0 g) in anhydrous N,N-dimethylformamide (32 ml) heated to 146° C. The reaction mixture was stirred at this temperature for 1 hour 30 minutes. After cooling, the mixture was poured onto ice and extracted with ethyl acetate (3×100 ml). The combined organic phases were washed with saturated NaCl solution (3×50 ml), dried over anhydrous sodium sulfate and evaporated under reduced pressure. The residue was chromatographed on a column of alumina (eluting with a 1/1 chloroform/petroleum ether mixture) to give 1.45 g (81.5%) of pure product as an oil.
$^1$H NMR (CDCl$_3$, δ ppm): 1.58-1.59 (m, 2H); 1.91-2.11 (m, 5H); 2.94-3.02 (m, 2H); 3.59 (s, 2H); 4.02 (s, 3H); 4.50 (d, 2H); 7.31-7.39 (m, 4H); 7.77 (m, 1H); 7.92 (2m, 2H).

8) 4-[(1-Piperid-4-yl)methyloxy]-2-methyl-2H-pyrrolo[3,4-c]-quinoline (Compound of Formula II: R1=CH$_3$; R2=H)
To a solution of the product prepared in Example 7 (0.35 mmol; 1.34 g) in methanol (150 ml) was added 10% palladium-on-charcoal (200 mg). The mixture was stirred under an H$_2$ atmosphere at room temperature and pressure for 4 days, a stream of H$_2$ being passed through every 3 hours and 10% palladium-on-charcoal (200 mg) being added every 24 hours. After filtering off the palladium on filter paper, the solvent was removed under reduced pressure to obtain a residue, which was chromatographed on a column of alumina (eluting with a 2/1 chloroform/methanol mixture). 410 mg (40%) of pure product were thus obtained as an oil.
$^1$H NMR (CDCl$_3$, δ ppm): 1.47-1.57 (m, 2H); 1.91-2.29 (m, 5H); 3.11-3.28 (m, 2H); 4.03 (s, 3H); 4.46-4.51 (d, 2H); 7.30-7.47 (m, 4H); 7.78 (m, 1H); 7.94 (m, 1H).

8a) Ethyl 4-(2-chloroethyl)benzenecarboxylate

To a suspension of 4-(2-chloroethyl)benzenecarboxylic acid (52.5 mmol; 9.7 g) in anhydrous ethanol (57 ml) was added concentrated sulfuric acid (3.0 ml). The mixture was stirred at reflux for 2 hours 30 minutes. After cooling, the ethanol was removed under reduced pressure and the crude product obtained was dissolved in chloroform (200 ml). The organic phase was washed first with 1N NaOH (100 ml) and then with saturated NaCl solution (3×100 ml). After drying over anhydrous sodium sulfate and removing the solvent under reduced pressure, 12.0 g (100%) of pure product were thus obtained as a pale yellow oil.
$^1$H NMR (CDCl$_3$, δ ppm): 1.42 (t, 3H); 2.74 (t, 2H); 3.34 (t, 2H); 4.39 (q, 2H); 7.55 (m, 2H); 8.04 (m, 2H).

8b) 4-(2-Bromoethyl)benzeneamine

To a solution of 4-nitro-1-(2-bromoethyl)benzene (13 mmol; 3.0 g) in ethyl acetate (200 ml) was added 10% palladium-on-charcoal (500 mg). The resulting suspension was placed under an H$_2$ atmosphere in a Parr hydrogenator at 70 psi at room temperature for 4 hours. At the end of this period, the suspension was filtered through a filter paper and the solvent was evaporated off under reduced pressure to give 2.81 g of amine (46.8%) as an oil, which was used for the following reaction without further purification.

8c) N-[4-(2-Bromoethyl)phenyl]acetamide

To a suspension of 4-(2-bromoethyl)benzeneamine prepared in Example 8b (1.0 g; 5 mmol) in pyridine (1.2 ml) and acetic anhydride (1.27 g; 12.4 mmol), placed in an ice bath for 30 minutes, was added 1N HCl. The mixture was extracted with ethyl acetate (3×200 ml). The combined organic phases were washed with saturated NaCl solution (3×300 ml), dried over anhydrous sodium sulfate and evaporated under reduced pressure. The crude product obtained was purified on a column of silica (eluting with ethyl acetate) to give 620 mg (51%) of product:
solid, m.p. 135-136° C. (benzene),
$^1$H NMR (CDCl$_3$, δ ppm): 2.25 (s, 3H); 3.19 (t, 2H); 3.59 (t, 2H); 7.22 (d, 2H); 7.50 (d, 2H).

8d) 4'-(2-Bromoethyl)methanesulfonanilide

To a solution of 4-aminophenylethyl bromide (5 mmol; 1.0 g) in anhydrous THF (25 ml) was added triethylamine (6.6 mmol; 0.744 g; 0.81 ml). To the mixture placed in an ice bath was added methanesulfonyl chloride (6 mmol, 0.687 g; 0.46 ml). The mixture was stirred at room temperature for 45 minutes and then diluted with water, acidified with 1N HCl to acidic pH, and extracted with ethyl acetate. The combined organic phases were washed with saturated NaCl solution and dried over anhydrous sodium sulfate. The solvent was removed under reduced pressure to give 1.18 g of crude product as a yellow oil. The crude product was chromatographed on a column of alumina (eluting with a 1/1 ethyl acetate/chloroform mixture) to give 580 mg (41%) of product having the following characteristics:
solid, m.p. 115-116° C. (toluene/hexane),
$^1$H NMR (CDCl$_3$, δ ppm): 3.07 (s, 3H); 3.21 (t, 2H); 3.61 (t, 2H); 6.40 (s, 1H); 7.25-7.29 (m, 4H).

8e) 4-(2-Bromoethyl)benzyl alcohol

To a suspension of LiAlH$_4$ (4.5 mmol; 0.172 g) in anhydrous THF (5.0 ml) cooled to 0° C. was added dropwise a solution of methyl 4-(2-bromoethyl)benzenecarboxylate (1.0 g; 4.1 mmol) in anhydrous THF (10.0 ml). The reaction mixture was stirred for 5 minutes at room temperature and, after adding ice, was filtered through a Büchner filter. The solvent was removed under reduced pressure and the residue was extracted with ethyl acetate (3×100 ml). The combined organic phases were washed with saturated NaCl solution, dried over sodium sulfate and evaporated under reduced pressure. 800 mg (82.6%) of pure product were thus obtained as an oil.
$^1$H NMR (CDCl$_3$, δ ppm): 3.22 (t, 2H); 3.62 (t, 2H); 4.72 (s, 2H); 7.25-7.39 (m, 4H).

8f) 4-(Methoxymethyl)phenylethyl bromide

To a suspension of 60% NaH in paraffin (13.9 mmol; 0.56 g) in THF (20 ml) cooled to 0° C. was first added, dropwise, a solution of 4-(2-bromoethyl)benzyl alcohol (9.25 mmol; 1.99 g) in THF (20 ml) in an ice bath, followed by iodomethane (13.9 mmol; 1.972 g; 0.86 ml). The mixture was stirred at room temperature for 1 hour 30 minutes, after which it was poured into water and extracted with ethyl acetate. The combined organic phases were washed with saturated NaCl solution (3×20 ml), dried over anhydrous sodium sulfate and evaporated under reduced pressure. The residue was chromatographed on a column of alumina, eluting with ethyl acetate, to give 1.38 g of product as an oil (65%).

$^1$H NMR (CDCl$_3$, δ ppm): 3.24 (t, 2H); 3.44 (s, 2H); 3.64 (t, 2H); 4.50 (s, 3H); 7.25-7.47 (m, 4H).

8g) Isochroman-1-one

To a solution of isochroman (5.0 g; 37.3 mmol) in dichloromethane (465 ml) stirred at room temperature was added, over 15 minutes, a homogeneous mixture of potassium permanganate and manganese dioxide (74.60 g) in a 1:3 ratio. The suspension obtained was left for 18 hours at room temperature. The suspension was filtered through a Büchner filter. The solvent was evaporated off under reduced pressure to give 4.42 g of crude product (80%), which was used for the following reaction without further purification.

8h) Methyl 2-(2-chloroethyl)benzenecarboxylate

A mixture of isochroman-1-one prepared in Example 8g (3.0 g; 20.2 mmol) and PCl$_5$ (20.4 mmol) was thermostatically maintained at 150° C. for 30 minutes. The POCl$_3$ thus formed was evaporated off, and methanol (15 ml) was then added. The reaction mixture was stirred at room temperature for 3 hours. The solvent was evaporated off to give a crude product, which was chromatographed on a column of silica, eluting with a 1/3 ethyl acetate/n-hexane mixture. 2.16 g (54%) of pure product were thus obtained as an oil.

$^1$H NMR (CDCl$_3$, δ ppm): 3.23 (t, 2H); 3.71 (t, 2H); 3.95 (s, 3H); 7.32-7.35 (m, 2H); 8.04-8.06 (m, 2H).

8i) 4-(2-Bromoethyl)benzenesulfonyl chloride

To a solution of 2-bromoethylbenzene (10.0 g; 54 mmol) in 16 ml of chloroform placed at a temperature of 0° C. was added dropwise a solution of chlorosulfonic acid (162 mmol, 18.87 g; 10.82 ml) in 11 ml of chloroform. After 15 minutes at 0° C., the reaction was maintained at room temperature for 3 hours. The reaction mixture was poured onto ice, and the aqueous phase was extracted with chloroform. The combined organic phases were washed with saturated sodium chloride solution and dried over anhydrous sodium sulfate. The solvent was evaporated off to give 12.34 g of crude product, which was purified by chromatography on a column of silica, eluting with chloroform (76% yield). The product obtained was used for the following reaction without further purification.

8j) 4-(2-Bromoethyl)benzenesulfonamide

To a solution of 4-chlorosulfonyl-1-(2-bromoethyl)benzene prepared in Example 81 (4.0 g; 15.2 mmol) in THF (1.76 ml; 15.2 mmol), cooled to 0° C., was added a solution of ammonium hydroxide (1.51 g; 30.4 mmol, 1.71 ml). The reaction took place immediately. The reaction mixture was diluted with water and filtered through a Gooch filter, to give 7.0 g of crude product, which was purified by chromatography on a column of silica, using chloroform as eluent. 570 mg (18% yield) of a product having the following characteristics were thus obtained:

white solid, m.p. 115-116° C. (ethanol), $^1$H NMR (CDCl$_3$, δ ppm): 3.24 (t, 2H); 3.58 (t, 2H); 7.37 (d, 2H); 7.91 (d, 2H).

9) 4-{[1-(2-(4-Morpholinyl)ethyl)piperid-4-yl]methyloxy}-2-methyl-2H-pyrrolo[3,4-c]quinoline (Compound of Formula I: R1=CH$_3$; R2=H; R3=CH$_2$—N-morpholine)

To a solution of the product prepared in Example 8 (1.3 mmol; 380 mg) in absolute ethanol (12 ml) were added 4-(2-chloroethyl)morpholine hydrochloride (1.3 mmol; 240 mg) and sodium bicarbonate (3.64 mmol; 310 mg). The mixture was stirred at reflux for 3 hours 15 minutes. After cooling, the solvent was removed under reduced pressure. The residue was taken up in water (50 ml) and extracted with ethyl acetate (3×50 ml). The combined organic phases were washed with saturated NaCl solution, dried over sodium sulfate and evaporated under reduced pressure to give 480 mg (90%) of product as an oil.

$^1$H NMR (CDCl$_3$, δ ppm): 1.61 (m, 2H); 1.89-1.97 (m, 3H); 2.13 (m, 2H); 2.56 (m, 4H); 2.63 (m, 4H); 3.09 (m, 2H); 3.78 (m, 4H); 4.03 (s, 3H); 4.49 (d, 2H); 7.32-7.46 (m, 4H); 7.78 (m, 1H); 7.93 (m, 1H).

9a) 4-{[1-(2-(4-Morpholinyl)ethyl)piperid-4-yl]methyloxy}-2-methyl-2H-pyrrolo[3,4-c]quinoline hydrochloride A solution of hydrochloric methanol was prepared by dropwise addition of acetyl chloride (1.68 mmol; 120 mg) to 3.2 ml of methanol cooled in an ice bath. The mixture was stirred gently for a few minutes, followed by dropwise addition of a solution of the amine prepared in Example 9 (0.76 mmol; 310 mg) in methanol (4.2 ml). Once the addition was complete, the mixture was stirred at 0° C. for 45 minutes, followed by addition of anhydrous ethyl ether (about 65 ml) until precipitation of the solvent was observed. After triturating for 2 days, the salt obtained was filtered off, washed with petroleum ether (3×2 ml) and dried under vacuum at 45° C. for 1 day. 150 mg (41%) of pure product having the following characteristics were thus obtained:

yellow solid, m.p. 190-192° C. (isopropyl ether/isopropanol), $^1$H NMR (DMSO-d6, δ ppm): 1.71-2.01 (m, 2H); 2.16-2.48 (m, 3H); 2.94-3.14 (m, 4H); 3.19-3.39 (m, 4H); 3.57 (t, J=7.31 Hz; 2H); 3.81 (d, J=12.57 Hz; 2H); 3.97 (t, J=4.38 Hz; 3H); 4.01 (s, 3H); 4.42 (d, J=5.70 Hz; 2H); 7.42 (d, J=1.75 Hz; 1H); 7.45-7.58 (m, 4H); 7.61 (s, 1H); 7.78 (d, J=7.75 Hz; 1H).

10) 4-[(1-(4-Nitrophenylethyl)piperid-4-yl)methyloxy]-2-methyl-2H-pyrrolo[3,4-c]quinoline (Compound I: R1=CH$_3$; R2=H; R3=CH$_2$—C$_6$H$_4$-(4-NO$_2$))

To a solution of the product prepared in Example 8 (2.2 mmol; 0.65 g) in DMF (5 ml) was added 4-nitrophenylethyl bromide (2.6 mmol; 0.61 g) and K$_2$CO$_3$ (6.6 mmol; 0.91 g). The mixture was stirred at 70° C. for 2 hours 45 minutes. After cooling, the mixture was diluted with water (20 ml) and extracted with ethyl acetate (3×30 ml). The combined organic phases were washed with saturated NaCl solution (3×50 ml), dried over sodium sulfate and evaporated under reduced pressure to give a crude product, which was chromatographed on a column of silica (eluting with a 10/1 chloroform/methanol mixture) to give 0.62 g (62%) of pure product having the following characteristics:

yellow solid, m.p. 157-159° C. (toluene/cyclohexane),
$^1$H NMR (CDCl$_3$, δ ppm): 1.65 (m, 2H); 2.00 (m, 3H); 2.19 (m, 2H); 2.72 (t, J=8.2 Hz; 2H); 3.02 (t, J=8.2 Hz; 2H); 3.12 (m, 2H); 4.03 (s, 3H); 4.53 (d, 2H); 7.32-7.47 (m, 6H); 7.78 (m, 1H); 7.93 (2dd, J=8.1 Hz; J=1.1 Hz; 2H); 8.20 (d, J=8.7 Hz; 2H).

11) 4-[(1-(4-Aminophenylethyl)piperid-4-yl)methyloxy]-2-methyl-2H-pyrrolo[3,4-c]quinoline (Compound of formula I: R1=CH$_3$; R2=H; R3=CH$_2$—C$_6$H$_4$-(4-NH$_2$))

To a solution of the product prepared in Example 10 (1.4 mmol; 0.61 g) in ethyl acetate (100 ml) was added 10% palladium-on-charcoal (200 mg). The mixture was stirred under an H$_2$ atmosphere at room temperature and pressure for 4 hours. A further portion of 10% palladium-on-charcoal (100 mg) was then added, and the mixture was left under an H$_2$ atmosphere at room temperature and pressure for 19 hours, a stream of H$_2$ being passed through every 3 hours. The mixture was then filtered under vacuum on a Merck RP18 cartridge to remove the palladium, and the solvent was removed under reduced pressure, to give 0.57 g (99%) of pure product having the following characteristics:

yellow solid, m.p. 150-152° C. (toluene/cyclohexane),
$^1$H NMR (CDCl$_3$, δ ppm): 1.69 (m, 2H); 1.98 (m, 3H); 2.21 (m, 2H); 2.69 (m, 2H); 2.87 (m, 2H); 3.20 (m, 2H); 3.64 (bs, 2H); 4.04 (s, 3H); 4.53 (d, 2H); 6.69 (d, J=8.4 Hz; 2H); 7.07 (d, J=8.4 Hz; 2H); 7.32-7.47 (m, 4H); 7.79 (dd, J=7.7 Hz, J=1.2 Hz; 2H); 7.93 (2dd, J=7.7 Hz; J=1.2 Hz; 2H).

11a) 4-[(1-(4-Aminophenylethyl)piperid-4-yl)methyloxy]-2-methyl-2H-pyrrolo[3,4-c]quinoline hydrochloride A solution of hydrochloric methanol was prepared by dropwise addition of acetyl chloride (1.86 mmol; 140 mg) to 7.0 ml of methanol cooled in an ice bath. The mixture was stirred gently for a few minutes, followed by dropwise addition of a solution of the amine prepared in Example 11 (0.84 mmol; 350 mg) in methanol (5.6 ml). Once the addition was complete, the mixture was stirred at 0° C. for 45 minutes, followed by addition of anhydrous ethyl ether (about 70 ml) until precipitation of the salt was observed. After triturating for 3 hours, the salt was filtered off, washed with ethyl ether (3×2 ml) and dried under vacuum at 45° C. for 2 days. 390 mg (95%) of pure product having the following characteristics were thus obtained:

yellow solid, m.p. 165-167° C. (isopropyl ether/isopropanol),
$^1$H NMR (DMSO-d6, δ ppm): 1.66-1.94 (m, 2H); 1.96-2.29 (m, 3H); 2.86-3.89 (m, 8H); 4.00 (s, 3H); 4.49 (d, J=6.04 Hz; 2H); 7.22-7.46 (m, 6H); 7.63-7.76 (m, 2H); 7.80 (d, J=1.83 Hz; 1H); 8.01 (dd, J=7.50; 1.65 Hz; 1H); 10.00 (bs, 3H); 10.68 (bs, 1H).

12) Ethyl 4-[2-[4-[O-(2-methyl-2H-pyrrolo[3,4-c]quinolin-4-yl]-methoxypiperid-1-yl]ethyl]benzoate (Compound of formula I: R1=CH$_3$; R2=H; R3=CH$_2$—C$_6$H$_4$-(4-CO$_2$Et))

A mixture of the product prepared in Example 8 (1.79 mmol; 0.53 g), ethyl 4-(2-chloroethyl)benzenecarboxylate prepared in Example 8a (8.97 mmol; 1.91 g), NaI (8.97 mmol; 1.34 g) and triethylamine (8.97 mmol; 0.91 g; 125 ml) in 2-butanone (22 ml) was stirred at reflux for 12 hours. After cooling, the mixture was poured into water (200 ml) and extracted with ethyl acetate (2×50 ml). The combined organic phases were extracted with 1N HCl (3×50 ml) to extract the final amine, in the form of the solid hydrochloride. The solid thus formed and the acidic phases were combined and treated with sodium carbonate to alkaline pH, and extracted again with ethyl acetate (3×50 ml). The organic phase was dried over anhydrous sodium sulfate and the solvent was removed under reduced pressure. The crude product thus obtained was chromatographed on a column of alumina (using chloroform as eluent) to give 430 mg (51%) of pure product having the following characteristics:

brown oil,
$^1$H NMR (CDCl$_3$, δ ppm): 1.44 (t, 3H); 1.65 (m, 2H); 1.98 (m, 3H); 2.18 (m, 2H); 2.70 (t, 2H); 2.97 (t, 2H); 3.14 (m, 2H); 4.01 (s, 3H); 4.42 (q, 2H); 4.52 (d, 2H); 7.32-7.46 (m, 6H); 7.78 (dd, J=8.1 Hz; J=1.1 Hz; 2H); 7.92 (dd, J=8.1 Hz; J=1.1 Hz; 2H); 8.02 (d, J=8.4 Hz; 2H).

12a) 4-[2-[4-[O-(2-Methyl-2H-pyrrolo[3,4-c]quinolin-4-yl]methoxypiperid-1-yl]ethyl]benzoic acid (Compound of formula I: R1=CH$_3$; R2=H; R3=CH$_2$—C$_6$H$_4$-(4-CO$_2$H))

To a solution of the product prepared in Example 12 (0.42 mmol; 0.2 g) in 2.4 ml of 1/1 THF/EtOH was added 1N NaOH (1.02 mmol, 1.0 ml). The mixture was stirred at room temperature for 17 hours. 1N HCl was then added to pH 7 and the solid thus formed was filtered off. 50 mg (27%) of pure final product were thus obtained.

Solid, m.p. 155-166° C. (ethanol),
$^1$H NMR (DMF-d7, δ ppm): 1.53 (m, 2H); 1.93 (m, 3H); 2.23 (m, 2H); 2.74 (m, 2H); 2.97 (m, 2H); 3.17 (m, 2H); 4.13 (s, 3H); 4.48 (d, 2H); 7.36 (m, 1H); 7.43 (m, 1H); 7.49 (d, J=8.1 Hz; 2H); 7.62 (d, J=1.9 Hz; 2H); 7.83 (d, J=1.9 Hz; 2H); 7.70 (m, 1H); 8.08 (m, 1H); 8.01 (d, J=8.1 Hz; 2H).

13) 4-[(1-(4-Acetamidophenylethyl)piperid-4-yl)methyloxy]-2-methyl-2H-pyrrolo[3,4-c]quinoline (Compound of formula I: R1=CH$_3$; R2=H; R3=CH$_2$—C$_6$H$_4$-(4-NHCOCH$_3$))

To a solution of the product prepared in Example 8 (1.5 mmol; 440 mg) in 2-butanone (20 ml) was added 4'-acetamido-2-bromoethylbenzene prepared in Example 8c (380 mg; 1.6 mmol). The mixture was refluxed for 1.5 hours. Triethylamine (161 mg; 1.6 mmol; 0.2 ml) was then added and the mixture was stirred for 1.5 hours, and then cooled to room temperature, diluted with water and extracted with 2-butanone. The organic phase was dried over anhydrous Na$_2$SO$_4$. Finally, the solvent was removed under reduced pressure to give a crude product, which was chromatographed on a column of Al$_2$O$_3$, eluting with ethyl acetate, to give 250 mg (40%) of product having the following characteristics:

solid, m.p. 145-146° C. (ethanol/hexane),
$^1$H NMR (CDCl$_3$, δ ppm): 1.64-1.76 (m, 4H); 1.99-2.02 (m, 2H); 2.23-2.24 (s, 3H); 2.93-2.95 (m, 2H); 2.97 (m, 2H); 3.26 (m, 2H); 4.04 (s, 3H); 4.53-4.54 (d, 2H); 7.18 (m, 1H); 7.22-7.24 (m, 2H); 7.35 (m, 1H); 7.39 (m, 3H); 7.77-7.79 (m, 1H); 7.93 (dd, 1H).

14) 4-[(1-(4-Methanesulfonylamidophenylethyl)piperid-4-yl)-methyloxy]-2-methyl-2H-pyrrolo[3,4-c]quinoline (Compound of formula I: R1=CH$_3$; R2=H; R3=CH$_2$—C$_6$H$_4$-(4-NHSO$_2$CH$_3$))

To a solution of the product prepared in Example 8 (1.17 mmol; 345 mg) in 2-butanone (14 mg) was added 4-(methanesulfonyl-amido)phenylethyl bromide prepared in Example 8d (360 mg, 1.29 mmol). The mixture was refluxed for 30 minutes, triethylamine (130 mg; 1.29 mmol; 0.2 ml) was then added and the mixture was stirred for 3 hours. The mixture was then brought to room temperature, diluted with water and extracted with 2-butanone. The organic phase was dried over anhydrous $Na_2SO_4$. The solvent was evaporated off under reduced pressure to give a crude product, which was chromatographed on a column of $Al_2O_3$, eluting with ethyl acetate. 330 mg of product (38%) having the following characteristics were thus obtained:

solid, m.p. 110-111° C. (toluene),
$^1$H NMR (CDCl$_3$, δ ppm): 1.31 (s, 1H); 1.70 (m, 2H); 1.86 (m, 3H); 2.23-2.24 (m, 4H); 2.67-2.69 (m, 2H); 2.87-2.89 (m, 2H); 3.04 (s, 3H); 3.13-3.16 (d, 2H); 4.04 (s, 3H); 4.52-4.53 (d, 2H); 7.34-7.35 (m, 1H); 7.39 (m, 1H); 7.44 (m, 1H); 7.77-7.80 (dd, 1H); 7.93 (dd, 1H).

15) 4-[(1-(4-Hydroxymethylphenylethyl)piperid-4-yl)methyloxy]-2-methyl-2H-pyrrolo[3,4-c]quinoline (Compound of formula I: R1=CH$_3$; R2=H; R3=CH$_2$—C$_6$H$_4$-(4-CH$_2$OH))

To a solution of the product prepared in Example 8 (3.3 mmol; 990 mg) in 2-butanone (33.5 ml) was added 4'-hydroxymethyl-2-bromoethylbenzene prepared in Example 8e (800 mg; 3.7 mmol). The solution was refluxed for 30 minutes, triethylamine (130 mg; 1.29 mmol; 0.2 ml) was then added and the mixture was stirred for 2 hours. A further portion of ethylamine (3.3 mmol; 0.33 g) was then added and, after a further two hours, the reaction mixture was brought to room temperature, diluted with water and extracted with 2-butanone. The organic phase was dried over anhydrous $Na_2SO_4$. The solvent was evaporated off under reduced pressure to give a crude product, which was chromatographed on a column of $Al_2O_3$, eluting with ethyl acetate. 0.67 g of product (48.5%) having the following characteristics was thus obtained:

solid, m.p. 145-146° C. (benzene/cyclohexane),
$^1$H NMR (CDCl$_3$, δ ppm): 1.31 (s, 1H); 1.64 (m, 2H); 1.84 (m, 3H); 1.99 (m, 3H); 2.10-2.15 (m, 3H); 2.64-2.68 (m, 2H); 2.87-2.92 (m, 2H); 3.14 (d, 2H); 4.03 (s, 3H); 4.53 (d, 2H); 4.72 (d, 2H); 7.26-7.28 (m, 2H); 7.32-7.38 (m, 5H); 7.44 (m, 1H); 7.78-7.80 (dd, 1H); 7.93 (dd, 1H).

16) 4-[(1-(4-Methoxymethylphenylethyl)piperid-4-yl)methyloxy]-2-methyl-2H-pyrrolo[3,4-c]quinoline (Compound of formula I: R1=CH$_3$; R2=H; R3=CH$_2$—C$_6$H$_4$-(4-CH$_2$OCH$_3$))

To a solution of the product prepared in Example 8 (3.3 mmol; 990 mg) in 2-butanone (33.5 ml) was added 4'-methoxymethyl-2-bromoethylbenzene prepared in Example 8f (800 mg; 3.7 mmol). The solution was refluxed for 30 minutes, triethylamine (130 mg; 1.29 mmol; 0.2 ml) was then added and the mixture was stirred for 1.5 hours. A further portion of ethylamine (3.3 mmol; 0.33 g) was then added and, after a further two hours, the reaction mixture was brought to room temperature, diluted with water and extracted with 2-butanone. The organic phase was dried over anhydrous $Na_2SO_4$. The solvent was evaporated off under reduced pressure to give a crude product, which was chromatographed on a column of $Al_2O_3$, eluting with ethyl acetate. 0.67 g of product (48.5%) having the following characteristics was thus obtained:

solid, m.p. 102-105° C. (isopropanol/hexane),
$^1$H NMR (CDCl$_3$, δ ppm): 1.61-1.68 (m, 2H); 1.96-1.99 (m, 3H); 1.84 (m, 3H); 1.99 (m, 3H); 2.10-2.15 (m, 3H); 2.64-2.68 (m, 2H); 2.11-2.14 (m, 2H); 2.64-2.68 (m, 2H); 2.87-2.92 (m, 2H); 3.12-3.14 (d, 2H); 3.44 (s, 3H); 4.03 (s, 3H); 4.48 (s, 2H); 4.51-4.54 (d, 2H); 7.25 (m, 2H); 7.32-7.34 (m, 4H); 7.36-7.39 (m, 2H); 7.42-7.45 (dd, 1H); 7.78-7.80 (dd, 1H); 7.92-7.94 (dd, 1H).

17) Methyl 2-[2-[4-[O-(2-methyl-2H-pyrrolo[3,4-c]quinolin-4-yl]-methoxypiperid-1-yl]ethyl]benzoate (Compound of formula I: R1=CH$_3$; R2=H; R3=CH$_2$—C$_6$H$_4$-(2-COOCH$_3$))

A mixture of the product prepared in Example 8 (3.31 mmol; 1.0 g) and methyl 2-(2-bromoethyl)benzenecarboxylate prepared in Example 8h (3.64 mmol; 0.74 g) in 2-butanone (35 ml) was refluxed for 30 minutes. After adding triethylamine (4.0 mmol; 0.4 g; 0.56 ml), the reaction mixture was stirred at reflux for 72 hours. After cooling, the mixture was diluted with water (50 ml) and then extracted with 2-butanone (2×50 ml). The combined organic phases were dried over anhydrous sodium sulfate and the solvent was removed under reduced pressure. The crude product thus obtained was purified by chromatography on a column of silica, eluting with ethyl acetate, to give 450 mg (30%) of pure product having the following characteristics:

yellow oil,
$^1$H NMR (CDCl$_3$, δ ppm): 1.28 (m, 1H); 1.65-1.68 (m, 2H); 1.96-1.98 (m, 3H); 2.26 (m, 2H); 2.70-2.74 (m, 2H); 3.17-3.29 (m, 4H); 3.92 (s, 3H); 3.99 (s, 3H); 4.50 (dd, 2H); 7.27-7.36 (m, 5H); 7.39-7.48 (m, 2H); 7.75 (dd, 1H); 7.88-7.92 (m, 2H).

17a) 2-[2-[4-[O-(2-Methyl-2H-pyrrolo[3,4-c]quinolin-4-yl]methoxypiperid-1-yl]ethyl]benzoic acid (Compound of formula I: R1=CH$_3$; R2=H; R3=CH$_2$—C$_6$H$_4$-(2-COOH))

To a solution of the product prepared in Example 17 (0.74 mmol; 0.34 g) in 3.4 ml of 1/1 THF/EtOH was added 1N NaOH (1.4 ml). The solution was stirred at room temperature for 12 hours, and glacial acetic acid was then added to pH 6. The solid obtained was filtered off to give a product (50% yield) having the following characteristics:

solid, m.p. 165° C. (ethyl acetate),
$^1$H NMR (DMF-d7, δ ppm): 1.30 (m, 2H); 1.51 (m, 2H); 1.79-1.82 (m, 1H); 2.51 (m, 5H); 2.87-2.92 (m, 2H); 3.07-3.10 (m, 2H); 3.98 (s, 3H); 4.35 (d, 2H); 7.23-7.37 (m, 5H); 7.57-7.62 (m, 3H); 7.72 (d, 1H); 7.96 (dd, 1H).

18) 4-[(1-(4-Sulfonamidophenylethyl)piperid-4-yl)methyloxy]-2-methyl-2H-pyrrolo[3,4-c]quinoline (Compound of formula I: R1=CH$_3$; R2=H; R3=CH$_2$—C$_6$H$_4$-(4-SO$_2$NH$_2$))

A mixture of the product prepared in Example 8 (3.37 mmol; 0.99 g) and 4-sulfonamido-1-(2-bromoethyl)benzene prepared in Example 8j (3.78 mmol; 1.00 g) in 2-butanone (34 ml) was refluxed for 10 minutes. After adding triethylamine (3.64 mmol; 0.188 g; 0.52 ml), the reaction mixture was stirred at reflux for 35 minutes. After cooling, the mixture was diluted with water (50 ml) and extracted with 2-butanone (2×50 ml). The combined organic phases were dried over anhydrous sodium sulfate and the solvent was removed under reduced pressure. A crude product was obtained, which was chromatographed on a column of alumina, eluting with ethyl acetate, and then on a column of silica, eluting with a 10/1 ethyl acetate/methanol mixture. 140 mg (11%) of product having the following characteristics were thus obtained:

orange-coloured solid; m.p. 169° C. with decomposition (toluene), $^1$H NMR (DMSO-d6, δ ppm): 1.18-1.36 (m, 2H); 1.85 (m, 3H); 2.01-2.26 (m, 2H); 3.07 (m, 2H); 3.71-3.92 (m, 2H); 3.98 (s, 3H); 4.43 (m, 2H); 7.27-7.36 (m, 2H); 7.55-7.60 (m, 3H); 7.73 (m, 2H); 7.97 (m, 2H).

FORMULATION EXAMPLES

Example 1

A tablet containing, as active principle, Compound 12a of the present invention, has the following composition:

| | |
|---|---|
| Active principle | 50 mg |
| Lactose monohydrate | 161 mg |
| Dibasic calcium phosphate dehydrate | 161 mg |
| Microcrystalline cellulose | 95 mg |
| Corn starch | 30 mg |
| Sodium carboxymethylstarch | 24 mg |
| Povidone | 11 mg |
| Magnesium stearate | 3 mg |

Example 2

An ampule containing, as active principle, Compound 12a of the present invention, has the following composition:

| | |
|---|---|
| Active principle | 25 mg |
| Sorbitol | qs iso-osmotic solution |
| Water | qs 100 ml |

Example 3

A pharmaceutical composition in the form of granules containing, as active principle, Compound 12a of the present invention, has the following composition:

| | |
|---|---|
| Active principle | 50 mg |
| Maltitol | 1300 mg |
| Mannitol | 2700 mg |
| Sucrose | 1000 mg |
| Citric acid | 20 mg |
| Aspartame | 20 mg |
| Flavourings | 200 mg |

The invention claimed is:

1. A compound of formula (I):

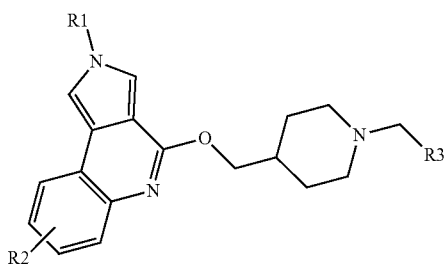

wherein:

R1 is a hydrogen atom, a linear or branched alkyl group, or an alkylalkoxy group;

R2 is a hydrogen atom, a halogen atom, or a linear or branched alkyl group, —CF$_3$, —OSO$_2$CF$_3$, —SO$_2$CH$_3$, —SO$_2$NHCH$_3$ or —NHSO$_2$CH$_3$;

R3 is (i) a hydrogen atom;

(ii) a linear or branched alkyl group;

(iii) an alkylalkoxy group;

(iv) an arylalkyl group or a heteroarylalkyl group, and the aryl or heteroaryl group is optionally substituted with one or two substituents, which are identical or different, selected from the group consisting of a halogen atom, an alkyl group containing 1-3 carbon atoms, an alkoxy group containing 1-3 carbon atoms, a hydroxyalkyl group containing 1-3 carbon atoms, —OH, —NR'R", —NO$_2$, —CF$_3$, —CO$_2$R', R'CON(R")—, R'SO$_2$N(R")—, and R'R"NSO$_2$—, in which R' and R", which are identical or different, are a hydrogen atom or an alkyl group containing 1-3 carbon atoms;

(v) R$^{iv}$R'NCO(CH$_2$)$_n$—, in which n is an integer from 0 to 2, and R$^{iv}$ and R$^v$, which are identical or different, are a hydrogen atom, an alkyl group containing 1-3 carbon atoms, an aryl group, or a heteroaryl group, optionally substituted with one or two substituents, which are identical or different, selected from the group consisting of a halogen atom, an alkyl group containing 1-3 carbon atoms, an alkoxy group containing 1-3 carbon atoms, a hydroxyalkyl group containing 1-3 carbon atoms, —OH, —NO$_2$, —NH$_2$, —CF$_3$, —CO$_2$H, —CO$_2$—C$_{1-3}$alkyl, —SO$_2$NH$_2$, and —NHSO$_2$—C$_{1-3}$alkyl; or (vi) C$_\gamma$—(CH$_2$)$_m$—, in which m is an integer from 0 to 2, and C$_\gamma$ is an alicyclic group containing 3 to 7 carbon atoms or a saturated 5- or 6-membered heterocyclic group containing at least one heteroatom selected from the group consisting of N and O, optionally N-substituted with an alkyl group containing 1 to 3 carbon atoms, or an acid-addition salt of the compound of formula (I) with a pharmaceutically acceptable organic or mineral acid, or a base-addition salt of the compound of formula (I) with a pharmaceutically acceptable organic or mineral base.

2. The compound, acid addition salt, or base addition salt according to claim 1, wherein R1 is a hydrogen atom or a linear or branched alkyl group,
R2 is a hydrogen atom, a halogen atom, —$CF_3$, —$OSO_2CF_3$, —$SO_2CH_3$, —$SO_2NHCH_3$, or —$NHSO_2CH_3$, and
R3 is
(i) a hydrogen atom;
(ii) a linear or branched alkyl group comprising 1-6 carbon atoms;
(iii) an arylalkyl group or a heteroarylalkyl group, in which the aryl or heteroaryl group is optionally substituted with one or two substituents, which are identical or different, selected from the group consisting of a halogen atom, an alkyl group containing 1-3 carbon atoms, an alkoxy group containing 1-3 carbon atoms, a hydroxyalkyl group containing 1-3 carbon atoms, —OH, —NR'R", —$NO_2$, —$CO_2R'$, R'CON(R")—, R'$SO_2$N(R")—, and R'R"N$SO_2$—, in which R' and R", which are identical or different, are a hydrogen atom or an alkyl group containing 1-3 carbon atoms;
(iv) $R^{iv}R'NCO(CH_2)_n$—, in which n is an integer from 0 to 2, and $R^{iv}$ and $R^v$, which are identical or different, are a hydrogen atom, an aryl group or a heteroaryl group; or
(v) $C_\gamma$—$(CH_2)_m$—, in which m is an integer from 0 to 2, and $C_\gamma$ is a saturated heterocyclic group selected from the group consisting of morpholine, piperidine, N-methylpiperazine, and pyrrolidine.

3. The compound, acid addition salt, or base addition salt according to claim 1, wherein
$R^1$ is a linear or branched alkyl group,
$R^2$ is a hydrogen atom, —$CF_3$, —$OSO_2CF_3$, —$SO_2CH_3$, —$SO_2NHCH_3$, or —$NHSO_2CH_3$, and $R^3$ is
(i) a linear or branched alkyl group containing 1-6 carbon atoms;
(ii) an arylalkyl group, in which the aryl group is optionally substituted with a substituent selected from the group consisting of an alkoxy group containing 1-3 carbon atoms, a hydroxyalkyl group containing 1-3 carbon atoms, —NR'R", —$CO_2R'$, R'CON(R")—, R'$SO_2$N(R")—, and R'R"N$SO_2$—, in which R' and R", which are identical or different, are a hydrogen atom or an alkyl group containing 1-3 carbon atoms;
(iii) $R^{iv}R'NCO(CH_2)_n$—, in which n is an integer from 0 to 2, and $R^{iv}$ and $R^v$, which are identical or different, are a hydrogen atom or an aryl group; or
(iv) $C_\gamma$—$(CH_2)_m$—, in which m is an integer from 0 to 2, and $C_\gamma$ is a morpholine or piperidine residue.

4. The compound, acid addition salt, or base addition salt according to claim 1, which is a compound selected from the group consisting of:
a compound (1) wherein $R^1$ is H, $R^2$ is Cl, and $R^3$ is $CH_3$;
a compound (2) wherein R1 is $C_2H_5$, R2 is $CH_3$, and R3 is $C_2H_5$;
a compound (3) wherein R1 is $CH_3$, R2 is H, and R3 is $CH_2CH_2CH_3$;
a compound (4) wherein R1 is $CH_3$, R2 is H, and R3 is $CH_2$—$C_6H_5$;
a compound (5) wherein R1 is $CH(CH_3)_2$, R2 is H, and R3 is $CH_2$—$C_6H_5$;
a compound (6) wherein R1 is $CH_3$, R2 is H, and R3 is CONH—$C_6H_5$;
a compound (7) wherein R1 is $CH_3$, R2 is H, and R3 is $C_6H_5$;
a compound (9) wherein R1 is $CH_3$, R2 is H, and R3 is $CH_2$—N-morpholine;
a compound (10) wherein R1 is $CH_3$, R2 is H, and R3 is $CH_2$—$C_6H_4$-(4-$NO_2$);
a compound (11) wherein R1 is $CH_3$, R2 is H, and R3 is $CH_2$—$C_6H_4$—(4-$NH_2$);
a compound (12) wherein R1 is $CH_3$, R2 is H, and R3 is $CH_2$—$C_6H_4$-(4-$COOC_2H_5$);
a compound (12a) wherein R1 is $CH_3$, R2 is H, and R3 is $CH_2$—$C_6H_4$-(4-COOH);
a compound (13) wherein R1 is $CH_3$, R2 is H, and R3 is $CH_2$—$C_6H_4$-(4-$NHCOCH_3$);
a compound (14) wherein R1 is $CH_3$, R2 is H, and R3 is $CH_2$—$C_6H_4$-(4-$NHSO_2CH_3$);
a compound (15) wherein R1 is $CH_3$, R2 is H, and R3 is $CH_2$—$C_6H_4$-(4-$CH_2OH$);
a compound (16) wherein R1 is $CH_3$, R2 is H, and R3 is $CH_2$—$C_6H_4$-(4-$CH_2COCH_3$);
a compound (17) wherein R1 is $CH_3$, R2 is H, and R3 is $CH_2$—$C_6H_4$-(2-$COOCH_3$);
a compound (17a) wherein R1 is $CH_3$, R2 is H, and R3 is $CH_2$—$C_6H_4$-(2-COOH);
a compound (18) wherein R1 is $CH_3$, R2 is H, and R3 is $CH_2$—$C_6H_4$-(4-$SO_2NH_2$);
a compound (19) wherein R1 is $C_2H_5$, R2 is H, and R3 is $CH_2$—$C_6H_4$-(4-$SO_2NHCH_3$);
a compound (20) wherein R1 is $CH_2OCH_3$, R2 is Br, and R3 is $CH_2$—N-pyrrolo-(3-OH);
a compound (21) wherein R1 is $CH_3$, R2 is Cl, and R3 is CONH—$C_6H_4$-(4-$NH_2$);
a compound (22) wherein R1 is $CH_2OC_2H_5$, R2 is $C_2H_5$, and R3 is $CH_2$—N-piperidine;
a compound (23) wherein R1 is $CH_3$, R2 is H, and R3 is $CH_2$—$C_6H_{11}$; and
a compound (24) wherein R1 is $CH_3$, R2 is H, and R3 is $CH_2$—$C_5H_9$,
or an acid addition salt of said compound or a base addition salt of said compound.

5. A pharmaceutical formulation, comprising an effective amount of a compound of formula (I) or the acid-addition or base-addition salt thereof according to claim 1, and at least one pharmaceutically acceptable excipient.

6. The pharmaceutical formulation according to claim 5, comprising an amount of the compound of formula (I) or the acid-addition or base-addition salt thereof so as to ensure a level of administration of between 0.001 and 100 mg/kg/day of compound of formula (I), expressed in free form.

7. A process for preparing a compound of formula (I) of claim 1

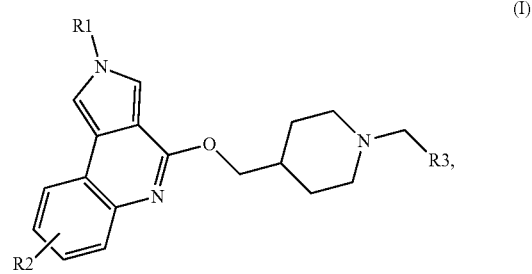

(I)

or a pharmaceutically acceptable acid-addition or base-addition salt thereof, the process comprising:

reacting a compound of formula (II):

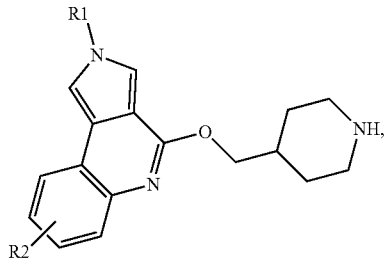

and a compound of formula (III):

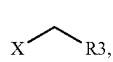

wherein X represents a halogen atom.

8. The process according to claim 7, wherein the reacting is performed in an organic solvent in the presence of an organic or mineral base compound.

9. The process according to claim 7, wherein the reacting is performed in the presence of an activating agent selected from the group consisting of potassium iodide, sodium iodide, caesium iodide, tetrabutylammonium iodide, and trimethylphenylammonium iodide.

10. A process for preparing a compound of formula (I) of claim 1

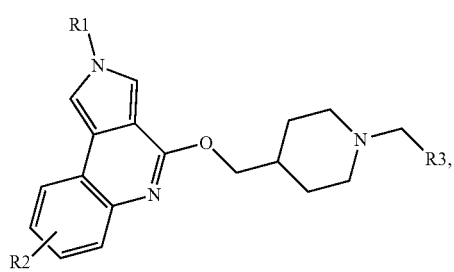

or a pharmaceutically acceptable acid-addition or base-addition salt thereof the process comprising:

reacting a compound of formula (IV):

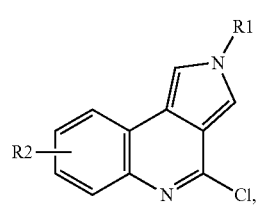

and a compound of formula (V):

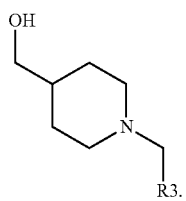

11. The process according to claim 10, wherein the reacting is performed in a dipolar aprotic organic solvent in the presence of a basic compound.

12. A process for preparing a compound of formula (II):

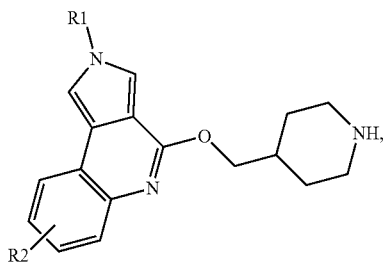

the process comprising:

(1) reacting a compound of formula (IV):

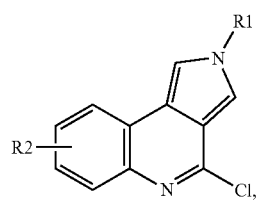

and a compound of formula (VI):

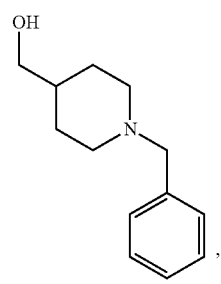

to give a compound of formula (VII):

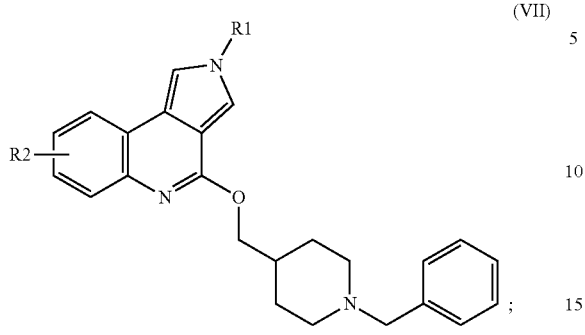

and (2) debenzylating the piperidine nitrogen of the compound of formula (VII) by hydrogenation, to give the compound of formula (II), wherein:
R1 is a hydrogen atom, a linear or branched alkyl group, or an alkylalkoxy group; and
R2 is a hydrogen atom, a halogen atom, or a linear or branched alkyl group, —$CF_3$, —$OSO_2CF_3$, —$SO_2CH_3$, —$SO_2NHCH_3$ or —$NHSO_2CH_3$.

13. The process according to claim 12, wherein
the reacting (1) is performed in a dipolar aprotic organic solvent selected from the group consisting of a ketone, tetrahydrofuran, dimethylformamide, dimethyl sulfoxide, dioxane, and acetonitrile, in the presence of a basic compound selected from the group consisting of sodium hydroxide and sodium hydride, and the debenzylating (2) is performed in an alcoholic solvent under a hydrogen atmosphere in the presence of a palladium-on-charcoal catalyst.

14. A compound of formula (II):

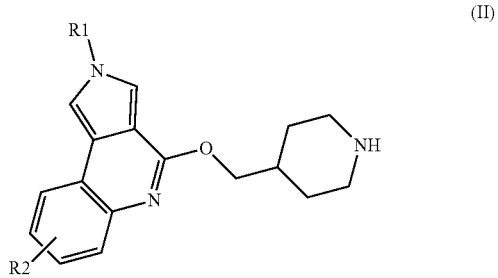

wherein:
R1 is a hydrogen atom, a linear or branched alkyl group, or an alkylalkoxy group; and
R2 is a hydrogen atom, a halogen atom, or a linear or branched alkyl group.

15. A method of preparing a pharmaceutical composition, the method comprising:
combining a compound, acid addition salt, or base addition salt of claim 1 with a pharmaceutically acceptable excipient.

16. The compound, acid addition salt, or base addition salt of claim 1, wherein the alkyl and/or alkoxy group of $R^1$ and/or $R^3$ (ii) and/or $R^3$ (iii) contains 1-6 carbon atoms.

17. The compound, acid addition salt, or base addition salt of claim 1, wherein the alkyl group of $R^2$ and/or the alky group of the arylalky or heteroarylalkyl group of $R^3$ (iv) contains 1-3 carbon atoms.

* * * * *

UNITED STATES PATENT AND TRADEMARK OFFICE
CERTIFICATE OF CORRECTION

PATENT NO. : 8,686,147 B2  
APPLICATION NO. : 13/003809  
DATED : April 1, 2014  
INVENTOR(S) : Alisi et al.

Page 1 of 1

It is certified that error appears in the above-identified patent and that said Letters Patent is hereby corrected as shown below:

On the title page, Item [30], the Foreign Application Priority Data has been omitted.
Item [30] should read:

-- [30]      Foreign Application Priority Data

Jul. 29, 2008    (EP) ...................... 08425516.5 --

Signed and Sealed this
Twenty-fourth Day of June, 2014

Michelle K. Lee
*Deputy Director of the United States Patent and Trademark Office*